(12) United States Patent
Kim et al.

(10) Patent No.: US 12,397,023 B2
(45) Date of Patent: Aug. 26, 2025

(54) COMPOSITION COMPRISING *Lactococcus chungangensis* FOR PREVENTION OR TREATMENT OF FATTY LIVER OR METABOLIC SYNDROME

(71) Applicant: CHUNG ANG UNIVERSITY INDUSTRY ACADEMIC COOPERATION FOUNDATION, Seoul (KR)

(72) Inventors: Won Yong Kim, Seoul (KR); Qi Zhang, Seoul (KR); Jong Hwa Kim, Seoul (KR)

(73) Assignee: CHUNG ANG UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 881 days.

(21) Appl. No.: 17/286,001

(22) PCT Filed: Oct. 18, 2019

(86) PCT No.: PCT/KR2019/013754
§ 371 (c)(1),
(2) Date: Mar. 24, 2022

(87) PCT Pub. No.: WO2020/080884
PCT Pub. Date: Apr. 23, 2020

(65) Prior Publication Data
US 2022/0257675 A1    Aug. 18, 2022

(30) Foreign Application Priority Data

Oct. 18, 2018 (KR) ........................ 10-2018-0124768

(51) Int. Cl.
*A61K 35/744* (2015.01)
*A61P 1/16* (2006.01)
*A61P 3/00* (2006.01)
*C12R 1/46* (2006.01)

(52) U.S. Cl.
CPC .............. *A61K 35/744* (2013.01); *A61P 1/16* (2018.01); *A61P 3/00* (2018.01); *C12R 2001/46* (2021.05)

(58) Field of Classification Search
None
See application file for complete search history.

(56) References Cited

U.S. PATENT DOCUMENTS

| 10,413,575 B2 | 9/2019 | Kim et al. |
| 2018/0085409 A1 | 3/2018 | Kim et al. |

FOREIGN PATENT DOCUMENTS

| KR | 10-1618330 | 5/2016 | |
| KR | 10-1723959 | 3/2017 | |
| KR | 10-2017-0109189 | 9/2017 | |
| KR | 10-2019-0111839 | 10/2019 | |
| WO | WO-2016068612 A1 * | 5/2016 | ........... A23C 19/076 |
| WO | WO-2019178309 A1 * | 9/2019 | ............. A23K 10/18 |

OTHER PUBLICATIONS

Cho, Characterization and Antimicrobial Effects of Lactococcus sp. Nob. CAU 28 Isolated from Activated Sludge Foam. Master's thesis, Chung-Ang University Graduate School. Dec. 2006. 69 pages.
Cho et al., *Lactococcus chungangensis* sp. nov., a lactic acid bacterium isolated from activated sludge foam. Intl J Sys Evol Microbiol. 2008;58:1844-9.
International Search Report for PCT/KR2019/013754, mailed Jan. 28, 2020, 3 pages.

* cited by examiner

*Primary Examiner* — Oluwatosin A Ogunbiyi
(74) *Attorney, Agent, or Firm* — Casimir Jones, S.C.; Jeffrey W. Childers

(57) ABSTRACT

The present invention relates to a *Lactococcus chungangensis* strain having preventive and reductive effects on fatty liver or metabolic syndrome. More particularly, the present invention relates to a composition at least one selected from the group consisting of the strain, a culture containing the strain, and a fermented material of the strain as an active ingredient for preventing, alleviating, and treating fatty liver or metabolic syndrome.

7 Claims, 36 Drawing Sheets

DMI  DMI + CAU 28

COMPOSITION COMPRISING *Lactococcus chungangensis* FOR PREVENTION OR TREATMENT OF FATTY LIVER OR METABOLIC SYNDROME

TECHNICAL FIELD

This application claims priority to Korean Patent Application No. 10-2018-0124768 filed on Oct. 18, 2018, and the entire specifications of which are incorporated herein by reference in their entireties.

The present invention relates to a composition for preventing or treating fatty liver or metabolic syndrome comprising *Lactococcus chungangensis*. Specifically, it relates to a composition for preventing or treating fatty liver or metabolic syndrome comprising at least one selected from the group consisting of a *Lactococcus chungangensis* strain, a culture of the strain, and a fermented product of the strain as an active ingredient.

BACKGROUND OF THE INVENTION

Metabolic syndrome refers to a case of having multiple cardiovascular risk factors such as hyperlipidemia, hypertension, glucose metabolism abnormality, blood coagulation abnormality, and obesity at the same time, and many of these risk factors promote the development of diabetes mellitus, atherosclerosis, and increase the risk of developing cardiovascular disease. Although the underlying mechanism of metabolic syndrome is not fully elucidated, it is known that obesity-related insulin resistance is the main cause. Insulin resistance is known to cause the onset of metabolic syndrome by causing hyperglycemia, hypertension, and dyslipidemia. That is, metabolic syndrome is characterized by an increase in blood pressure, an increase in plasma glucose and an increase in triglycerides, an increase in low-density lipoprotein cholesterol (LDL) and a decrease in high-density lipoprotein cholesterol (HDL).

Obesity is a metabolic disease caused by an imbalance in the intake and consumption of calories, and refers to a condition in which adipose tissue is abnormally increased due to excess calories. Fatty acids produced in adipose tissue accumulated through obesity increase the concentration of fatty acids in the blood and lower the insulin utilization rate in the liver and muscles. When blood fatty acids increase, the cells accept fatty acids instead of glucose, which makes it difficult for glucose to flow, leading to hyperglycemia, and a high blood glucose concentration stimulates the beta cells of the pancreas to secrete insulin, leading to more insulin secretion, resulting in increased insulin resistance.

On the other hand, obese people have higher cholesterol or triglyceride levels than those of normal weight, so they are more likely to develop hyperlipidemia. In particular, studies have found that abdominal obesity increases the risk of pancreatic cancer. Abdominal obesity occurs because the basal metabolic rate is lowered due to wrong eating habits, unrestricted life, excessive stress, lack of exercise, etc. In particular, abdominal obesity is closely related to drinking, smoking, and high-fat food intake, so it is easily seen in middle-aged working men.

Currently, as a treatment for obesity, exercise therapy, drug therapy, liposuction, or gastrectomy are used. However, busy modern people have a problem that it is difficult to exercise regularly, drug therapy has several side effects such as abdominal pain, steatorrhea, vomiting, leg pain, etc., and liposuction and gastrectomy have problems with poor safety. Simvastatin is a cholesterol-lowering agent generally used to treat hypercholesterolemia, and is known to exhibit anti-inflammatory effects in metabolic syndrome by reducing plasma release of anti-inflammatory cytokines (Devaraj et al., 2006).

It is known that nonalcoholic fatty liver lesions are associated with metabolic syndrome such as obesity, adult-type diabetes, and hyperlipidemia. If you continue to consume excessive calories, fat accumulates in the body fat cells and liver, fatty liver is diagnosed when excess fat (mainly triglycerides) accumulates in the liver and, in general, more than 5% of the liver's weight is accumulated. It is known that the liver secretes harmful cytokines from the increased fat and progresses to steatohepatitis and cirrhosis. Adult-type diabetes, which is caused by resistance to insulin secreted by the body, is also known as a cause of fatty liver. Increased insulin due to insulin resistance not only lowers blood sugar but also acts to store fat in the liver, causing fatty liver. It is also known that hyperlipidemia, in which the amount of total cholesterol or triglycerides in blood vessels is increased beyond normal values, lowers the liver's detoxification and lipolysis functions, causing fatty liver.

Enzymes present in hepatocytes are mainly released into the blood when hepatocytes are damaged, resulting in increased blood levels. As the concentration of AST (aspartate aminotransferase) and ALT (alanine aminotransferase) changes when hepatocytes are damaged, the blood concentration of AST (aspartate aminotransferase), ALT (alanine aminotransferase), ALP (Alkaline phosphatase), GGT (Gamma-Glutamyl Transferase) enzymes is mainly checked to determine whether there is any abnormality in liver function.

In the case of modern people, obesity or metabolic syndrome patients are rapidly increasing due to excessive intake of fat components in their diet. Obesity or metabolic syndrome is not only a problem in itself, but as the condition continues, various diseases and complications such as high blood pressure, hyperinsulinemia, hyperlipidemia, fatty liver, arteriosclerosis, diabetes, and cardiovascular disease occur, so it is even more dangerous because it ultimately shortens life. Since the socioeconomic cost is enormous, there is a lot of interest in the treatment of obesity or metabolic syndrome worldwide, but an effective treatment for metabolic syndrome is still insufficient. Therefore, it is very necessary to develop a material that can effectively prevent and treat it.

DETAILED DESCRIPTION OF THE INVENTION

Technical Problem

Accordingly, as a result of careful efforts to develop new materials that can prevent or treat metabolic syndrome, the present invention was completed by discovering that the *Lactococcus chungangensis* strain, the culture of the strain, and the fermented product of the strain had various effects such as obesity suppression, insulin resistance improvement, and hepatoprotective effect.

Accordingly, an object of the present invention is to provide a pharmaceutical composition for the prevention or treatment of fatty liver or metabolic syndrome comprising at least one selected from the group consisting of a *Lactococcus chungangensis* strain, a culture containing of the strain and a fermented material of the strain as an active ingredient In addition, an object of the present invention is to provide a pharmaceutical composition for preventing or treating fatty liver or metabolic syndrome consisting of at least one selected from the group consisting of a *Lactococcus chungangensis* strain, a culture containing of the strain and a fermented material of the strain.

In addition, an object of the present invention is to provide a pharmaceutical composition for preventing or treating fatty liver or metabolic syndrome essentially consisting of at least one selected from the group consisting of a *Lactococcus chungangensis* strain, a culture containing of the strain and a fermented material of the strain.

Another object of the present invention is to provide a food composition for preventing or improving fatty liver or metabolic syndrome comprising at least one selected from the group consisting of a *Lactococcus chungangensis* strain, a culture containing of the strain, and a fermented material of the strain as an active ingredient.

In addition, another object of the present invention is to provide a food composition for preventing or improving fatty liver or metabolic syndrome consisting of at least one selected from the group consisting of a *Lactococcus chungangensis* strain, a culture containing of the strain, and a fermented material of the strain.

In addition, another object of the present invention is to provide a food composition for preventing or improving fatty liver or metabolic syndrome essentially consisting of at least one selected from the group consisting of a *Lactococcus chungangensis* strain, a culture containing of the strain, and a fermented material of the strain.

Another object of the present invention is to provide use of a composition comprising at least one selected from the group consisting of a *Lactococcus chungangensis* strain, a culture containing of the strain, and a fermented material of the strain as an active ingredient for preparing an agent for preventing or treating fatty liver or metabolic syndrome.

Another object of the present invention is to provide a method for treating fatty liver or metabolic syndrome comprising administering an effective amount of a composition comprising at least one selected from the group consisting of a *Lactococcus chungangensis* strain, a culture containing of the strain, and a ferment material of the strain as an active ingredient to a subject in need thereof.

Technical Solution

In order to achieve the above object, the present invention provides a pharmaceutical composition for the prevention or treatment of fatty liver or metabolic syndrome comprising at least one selected from the group consisting of a *Lactococcus chungangensis* strain, a culture containing of the strain and a fermented material of the strain as an active ingredient.

The present invention also provides a pharmaceutical composition for the prevention or treatment of fatty liver or metabolic syndrome consisting of at least one selected from the group consisting of a *Lactococcus chungangensis* strain, a culture containing of the strain and a fermented material of the strain.

The present invention also provides a pharmaceutical composition for the prevention or treatment of fatty liver or metabolic syndrome essentially consisting of at least one selected from the group consisting of a *Lactococcus chungangensis* strain, a culture containing of the strain and a fermented material of the strain.

In order to achieve another object of the present invention, the present invention provides a food composition for preventing or improving fatty liver or metabolic syndrome comprising at least one selected from the group consisting of a *Lactococcus chungangensis* strain, a culture containing of the strain, and a fermented material of the strain as an active ingredient.

The present invention provides a food composition for preventing or improving fatty liver or metabolic syndrome consisting of at least one selected from the group consisting of a *Lactococcus chungangensis* strain, a culture containing of the strain, and a fermented material of the strain.

The present invention provides a food composition for preventing or improving fatty liver or metabolic syndrome essentially consisting of at least one selected from the group consisting of a *Lactococcus chungangensis* strain, a culture containing of the strain, and a fermented material of the strain.

In order to achieve another object of the present invention, the present invention provides use of a composition comprising at least one selected from the group consisting of a *Lactococcus chungangensis* strain, a culture containing of the strain, and a fermented material of the strain as an active ingredient for preparing an agent for preventing or treating fatty liver or metabolic syndrome.

In order to achieve another object of the present invention, the present invention provides a method for treating fatty liver or metabolic syndrome comprising administering an effective amount of a composition comprising at least one selected from the group consisting of a *Lactococcus chungangensis* strain, a culture containing of the strain, and a ferment material of the strain as an active ingredient to a subject in need thereof.

Hereinafter, the present invention will be described in detail.

In the present invention, the *Lactococcus chungangensis* may be characterized in that the accession number is KCTC 12684BP, but is not limited thereto.

The strain of the present invention, *Lactococcus chungangensis*, is a strain isolated from wastewater of a wastewater treatment plant, and taxonomically corresponds to Gram-positive cocci. This strain is a new strain newly discovered by the inventor of the present invention, and as a result of cell morphological and biochemical tests, it was identified as a strain belonging to the genus *Lactococcus*, and was deposited at the Korea Microbial Resource Center in 2008 (Accession No.: KCTC 12684BP). In addition, *Lactococcus chungangensis* is a Gram-positive cocci and does not form spores and mycelium, and is characterized by occurring singly or in pairs in the form of short chains or irregular clusters, and a more detailed description of this strain can be found in "International Journal of Systematic and Evolutionary Microbiology (2008), 58, 18441849".

The composition of the present invention, including the *Lactococcus chungangensis* strain, since the microbial enzyme is present in the culture medium or culture supernatant of the strain, the strain, its culture medium, or a composition comprising a culture supernatant is included in the scope of rights. *Lactococcus chungangensis* can be removed from the culture medium, and the preferred culture medium is the supernatant after centrifugation. The culture solution may include both the concentrated solution of the culture solution and the dried product of the culture solution. In addition, the composition of the present invention may include live *Lactococcus chungangensis*, crushed cell wall fraction, dead or dried bacteria as an active ingredient, and may further include an excipient or carrier.

In the present invention, the fermented material refers to the product of fermenting natural products, dairy products, etc. using at least one selected from the group consisting of

*Lactococcus chungangensis* strain, the culture containing of the strain, a concentrate of the culture and a dried product of the culture as a starter.

The method for culturing *Lactococcus chungangensis* of the present invention is not particularly limited, and can be performed by a regular method. For example, it is possible to recover the cells by culturing in a medium in which microorganisms can proliferate and using means such as centrifugation.

The composition comprising *Lactococcus chungangensis* of the present invention as an active ingredient has an activity of improving fatty liver or various diseases of metabolic syndrome, for example, obesity, dyslipidemia, hyperlipidemia, diabetes or insulin resistance syndrome. The composition of the present invention can prevent or treat metabolic syndrome by various activities.

As used herein, the term 'insulin resistance syndrome' is a generic term for diseases induced by the insulin resistance, and means a disease characterized by cellular resistance to insulin action, hyperinsulinemia, increasing in very low density lipoprotein (VLDL) and triglycerides, decreasing in high density lipoprotein (HDL) and hypertension etc., and it is a concept recognized as a risk factor for cardiovascular disease and type 2 diabetes (Reaven G M., Role of insulin resistance in human disease, Diabetes, 37:1595-607(1988)). It is also known that insulin resistance increases intracellular oxidative stress along with risk factors such as high blood pressure, diabetes, and smoking, and induces an inflammatory response by changing the signaling system to advance atherosclerosis (Freeman B A et al., Biology of disease: free radicals and tissue injury, Lab. Invest. 47:412-26(1982), Kawamura M et al., Pathophysiological concentrations of glucose promote oxidative modification of low density lipoprotein by a superoxide dependent pathway, J. Clin. Invest. 94:771-8(1994)).

The composition of the present invention can be applied to the prevention or treatment of insulin resistance syndrome, more preferably obesity, hypertension, arteriosclerosis, hyperlipidemia, hyperinsulinemia, nonalcoholic fatty liver or type 2 diabetes caused by insulin resistance.

According to an embodiment of the present invention, the result of oral administration of *Lactococcus chungangensis* lyophilizates (same as freeze-dried cells) or cream cheese containing the same to a high-fat diet C57BL/6J mouse animal model, it was shown to have a preservative effect on the glucose tolerance function induced in obesity by reducing the blood glucose level. By confirming the preservation effect of *Lactococcus chungangensis* on the glucose tolerance function resulting from obesity, it was found that *Lactococcus chungangensis* could be usefully used for the prevention or treatment of metabolic syndrome including insulin resistance risk factors.

In addition, in another embodiment of the present invention, it was confirmed that the effect of inhibiting weight gain induced by a high-fat diet in the C57BL/6J mouse animal model was significantly shown in the experimental group in which the *Lactococcus chungangensis* was orally administered, and it has been shown to have the effect of reducing the fat in the tissues produced by obesity. Therefore, it was confirmed that there is an effect of preventing or treating obesity or obesity-related metabolic syndrome in the present invention. According to an embodiment of the present invention, the blood cholesterol level due to obesity was higher in the positive control group fed the high-fat diet than the negative control group of the C57BL/6J mouse animal model fed the normal diet, but it was confirmed that the cholesterol level was significantly lower in the experimental group in which *Lactococcus chungangensis* or cream cheese containing the same was orally administered along with a high-fat diet.

Excess fat caused by high-fat diet intake causes fatty liver, and non-alcoholic fatty liver causes abnormality and damage to liver function. The experimental group administered orally administered *Lactococcus chungangensis* showed significantly lower levels of AST and ALT compared with the positive control group. Therefore, it was found that the *Lactococcus chungangensis* of the present invention has an effect of inhibiting liver function damage.

In addition, according to another embodiment of the present invention, it was confirmed that there is an effect of preventing or treating obesity or hyperlipidemia as *Lactococcus chungangensis* was shown to have an effect of reducing fat and cholesterol levels in a hyperlipidemic BALB/c mouse animal model induced by a high-fat diet. In the present invention, the obesity may preferably be abdominal obesity, but is not limited thereto.

The pharmaceutical composition according to the present invention may be formulated in a suitable form together with a pharmaceutically acceptable carrier, and may further contain an excipient or diluent. As used herein, 'pharmaceutically acceptable' refers to a non-toxic composition that is physiologically acceptable and does not normally cause allergic reactions or similar reactions such as gastrointestinal disorders and dizziness when administered to humans.

The pharmaceutically acceptable carrier may further include, for example, a carrier for oral administration or a carrier for parenteral administration. Carriers for oral administration may include lactose, starch, cellulose derivatives, magnesium stearate, stearic acid, and the like. In addition, the carrier for parenteral administration may include water, a suitable oil, saline, aqueous glucose and glycol, and the like, and may further include a stabilizer and a preservative. Suitable stabilizers include antioxidants such as sodium bisulfite, sodium sulfite or ascorbic acid. Suitable preservatives include benzalkonium chloride, methyl- or propyl-paraben and chlorobutanol. The pharmaceutical composition of the present invention may further include a lubricant, a wetting agent, a sweetening agent, a flavoring agent, an emulsifying agent, a suspending agent, etc. in addition to the above components. Other pharmaceutically acceptable carriers and agents may refer to those known in the art.

The composition of the present invention can be administered to mammals including humans by any method. For example, it may be administered orally or parenterally. The parenteral administration method is not limited thereto, but may be intravenous, intramuscular, intraarterial, intramedullary, intrathecal, intracardiac, transdermal, subcutaneous, intraperitoneal, intranasal, intestinal, topical, sublingual or rectal administration.

The pharmaceutical composition of the present invention may be formulated as an agent for oral administration or parenteral administration according to the administration route as described above.

In the case of a formulation for oral administration, the composition of the present invention may be formulated as a powder, granules, tablets, pills, dragees, capsules, liquids, gels, syrups, slurries, suspensions etc. using methods known in the art. For example, oral agents may be prepared by combining the active ingredient with a solid excipient and then grinding it and after adding suitable adjuvant, tablets or dragees can be obtained by processing into a granule mixture.

Examples of suitable excipients may include sugars including lactose, dextrose, sucrose, sorbitol, mannitol, xylitol, erythritol and maltitol, and the like, starches including corn starch, wheat starch, rice starch and potato starch and the like, cellulose including cellulose, methylcellulose, sodium carboxymethylcellulose and hydroxypropylmethylcellulose, and the like, fillers such as gelatin, polyvinylpyrrolidone, and the like. In addition, cross-linked polyvinylpyrrolidone, agar, alginic acid or sodium alginate and the like may be added as a disintegrant if necessary. Furthermore, the pharmaceutical composition of the present invention may further include an anti-aggregating agent, a lubricant, a wetting agent, a flavoring agent, an emulsifying agent, and an antiseptic agent and the like.

Agents for parenteral administration may be formulated in the form of injections, creams, lotions, external ointments, oils, moisturizers, gels, aerosols and nasal inhalants by methods known in the art. These formulations are described in formulary commonly known in all pharmaceutical chemistry.

The total effective amount of the composition of the present invention may be administered to a patient as a single dose, and may be administered by a fractionated treatment protocol in which multiple doses are administered for a long period of time. The pharmaceutical composition of the present invention may vary the content of the active ingredient depending on the severity of the disease. Preferably, the preferred total dose of the pharmaceutical composition of the present invention may be about 0.01 µg to 10,000 mg, most preferably 0.1 µg to 1000 mg per kg of patient body weight per day.

However, the dosage of the pharmaceutical composition is determined the effective dosage for the patient in consideration of various factors such as the age, weight, health status, sex, disease severity, diet and excretion rate and the like of the patient as well as the formulation method, route of administration and number of treatments, so that is determined, in consideration of these points, those of ordinary skill in the art will be able to determine an appropriate effective dosage of the composition of the present invention. The pharmaceutical composition according to the present invention is not particularly limited in its formulation, administration route and administration method as long as the effect of the present invention is exhibited.

The present invention also provides a food composition for improving obesity comprising at least one selected from the group consisting of a *Lactococcus chungangensis* strain, a culture containing of the strain, and a fermented material of the strain as an active ingredient.

In the present invention, the food may be a fermented food or cheese containing *Lactococcus chungangensis*, but is not limited thereto.

Preferably, the fermented food may be a fermented food prepared by using at least one selected from the group consisting of a *Lactococcus chungangensis* strain, a culture containing of the strain, the concentrate of the culture containing and a dried product of the culture containing as a starter.

As used herein, the term 'starter' refers to an agent containing microorganisms involved in the fermentation of food, and refers to a microorganism that predominantly grows in aged food by adding it during the manufacture of fermented food, and refers to an agent essentially containing a microorganism, that is, *Lactococcus chungangensis*, which provides not only constant control of the taste of fermented food but also excellent sensuality.

In the present invention, the fermented food includes beer, fruit wine, medicinal wine, vinegar, soy sauce, soybean paste, cheonggukjang, gochujang, kimchi, pickles, miso, natto, salted seafood, seafood, fermented milk products ham or sausage, and may preferably be a fermented dairy product such as cheese or yogurt, but is not limited thereto.

Such a food composition may contain various flavoring agents or natural carbohydrates as an additional ingredient, like a conventional food composition, in addition to containing the *Lactococcus chungangensis* strain, a culture containing of the strain, a concentrate of the culture containing or the dried product of the culture containing as an active ingredient. Examples of the above-mentioned natural carbohydrates include monosaccharides such as glucose, fructose and the like; disaccharides such as maltose, sucrose and the like; and polysaccharides such as conventional sugars such as dextrin and cyclodextrin, and sugar alcohols such as xylitol, sorbitol, and erythritol. The above-mentioned flavoring agents can advantageously use natural flavoring agents (taumatin), *Stevia* extracts (e.g., rebaudioside A, glycyrrhizin, etc.) and synthetic flavoring agents (saccharin, aspartame, etc.).

The food composition of the present invention may be formulated in the same manner as the pharmaceutical composition and used as a functional food or added to various foods. Foods to which the composition of the present invention can be added include, for example, beverages, meat, chocolate, food, confectionery, pizza, ramen, other noodles, gum, candy, ice cream, alcoholic beverages, vitamin complexes, and health supplements and the like.

In addition, the food composition may contain various nutrients, vitamins, minerals (electrolytes), synthetic and natural flavoring agents, such as flavoring agents, coloring agents and thickening agents (cheese, chocolate, etc.), pectic acid and its salts, alginic acid and its salts, organic acids, protective colloidal thickeners, pH Regulators, stabilizers, preservatives, glycerin, alcohol, a carbonation agent used in carbonated beverages, and the like, other than the *Lactococcus chungangensis* strain, a culture containing of the strain, a concentrate of the culture containing or the dried product of the culture as an active ingredient. In addition, the food composition of the present invention may contain natural fruit juice and pulp for the production of fruit juice beverages and vegetable beverages.

The food composition of the present invention may be a health functional food for improving obesity comprising at least one selected from the group consisting of a *Lactococcus chungangensis*, a culture containing of the strain, a concentrate of the culture containing or the dried product of the culture as an active ingredient.

In the present invention, the term 'health functional food' refers to a food manufactured and processed using raw materials or ingredients useful for the human body according to Health Functional Food Act No. 6727, it refers to ingestion for the purpose of obtaining useful effects for health purposes such as regulating nutrients for the structure and function of the human body or physiological effects.

The health functional food of the present invention may include conventional food additives, unless otherwise specified, the suitability as a food additive is judged according to the standards and standards for the relevant item in accordance with the general rules and general test methods of the Food Additives Code approved by the Ministry of Food and Drug Safety.

The items listed in the 'Food Additives Codex' include, for example, natural additives such as ketones, chemical compounds such as glycine, calcium citrate, nicotinic acid, and cinnamic acid; dark pigment, licorice extract, crystalline cellulose, high amount of pigment, and guar gum and the like; and mixed agents such as sodium L-glutamate agents, noodles-added alkalis, preservatives, and tar dye agents and the like. For example, a health functional food in tablet form is granulated by a conventional method by mixing the active ingredient of the present invention with an excipient, binder, disintegrant and other additives, then can be compression molded by adding a lubricant and the like, or can be directly compression molded of the mixture. In addition, the health functional food in the form of tablets may contain a corrosive agent and the like, if necessary.

Among health functional foods in the form of capsules, hard capsules can be prepared by filling a mixture of the active ingredient of the present invention with additives such as excipients in ordinary hard capsules, and soft capsules can be prepared by filling a mixture mixed with additives such as excipients in a capsule base such as gelatin. The soft capsules may contain a plasticizer such as glycerin or sorbitol, a colorant, a preservative, and the like, if necessary.

A health functional food in the form of a pill can be prepared by molding a mixture of the active ingredient of the present invention with an excipient, a binder, a disintegrant, etc. by a known method, if necessary, it can be coated with sucrose or other skinning agents, alternatively, the surface may be coated with a material such as starch or talc.

The health functional food in the form of granules can be prepared in a granular form by a conventionally known method by mixing the active ingredient of the present invention with an excipient, a binder, a disintegrant, and the like. If necessary, it may contain a flavoring agent, a flavoring agent, and the like.

The health functional food may be beverages, meat, chocolate, foods, confectionery, pizza, ramen, other noodles, gums, candy, ice cream, alcoholic beverages, vitamin complexes, and health supplements and the like.

In addition, the present invention provides an use of a composition comprising at least one selected from the group consisting of a *Lactococcus chungangensis* strain, a culture containing of the strain, and a fermented material of the strain as an active ingredient for preparing an agent for preventing or treating fatty liver or metabolic syndrome.

In addition, the present invention provides a method for treating fatty liver or metabolic syndrome comprising administering an effective amount of a composition comprising at least one selected from the group consisting of a *Lactococcus chungangensis* strain, a culture containing of the strain, and a ferment material of the strain as an active ingredient to a subject in need thereof.

The 'effective amount' of the present invention refers to an amount that, when administered to a subject, exhibits the effect of improving, treating, preventing, detecting, diagnosing, or inhibiting or reducing fatty liver or metabolic syndrome, and the 'subject' may be an animal, preferably an animal including a mammal, particularly a human, and it may be a cell, tissue, organ, or the like derived from an animal. The subject may be a patient in need of the effect.

The 'treatment' of the present invention refers comprehensively to improving the symptoms of fatty liver or metabolic syndrome or the disease, this may include curing, substantially preventing, or ameliorating the condition of fatty liver or metabolic syndrome, and include, but not limited to, alleviating, curing or preventing one or most of the symptoms resulting from the disease.

In the present invention, the term 'comprising' is used the same as 'comprising' or 'characterized', for a composition or method, additional component elements or method steps not mentioned are not excluded. The term 'consisting of' means excluding additional elements, steps, or ingredients that are not otherwise specified. The term 'essentially consisting of' means including, in the scope of a composition or method, a component element or step that does not substantially affect its basic properties in addition to the described component element or step.

Advantageous Effect

Accordingly, the present invention provides a pharmaceutical composition for the prevention or treatment of fatty liver or metabolic syndrome comprising at least one selected from the group consisting of a *Lactococcus chungangensis* strain, a culture containing of the strain and a fermented material of the strain as an active ingredient. The composition comprising *Lactococcus chungangensis* of the present invention as an active ingredient can be usefully used for preventing and treating fatty liver or metabolic syndrome disease because it is excellent in preventing or treating fatty liver or metabolic syndrome, and reduces blood glucose levels and reduces insulin resistance, and has the effect of preserving glucose tolerance function, and has excellent weight gain inhibitory effect and liver damage inhibition ability.

BRIEF DESCRIPTION OF THE DRAWINGS

FIG. 4a shows the blood glucose concentration measured by OGTT at each time point after glucose ingestion, FIG. 4b shows the AUC calculated from OGTT data for 0-120 min after glucose uptake. Differences between means compared to positive controls were assessed using ANOVA. *$P<0.05$, $P<0.005$, *$P<0.0005$, ****$P<0.0001$.

FIG. 5a is the blood glucose concentration measured by ITT at each time point after insulin injection, FIG. 5b shows AUC calculated from ITT data for 0-120 min after insulin injection. Differences between means compared to positive controls were assessed using ANOVA. *P<0.05, P<0.005, *P<0.0005.

FIG. 6a is leptin, FIG. 6b is adiponectin, FIG. 6c is TNF-α, FIG. 6d is IL-β, FIG. 6e is IL-6, FIG. 6f is the serum level of IFN-γ. Differences between means compared to positive controls were assessed using ANOVA. *P<0.0005; **P<0.0001.

MODE FOR CARRYING OUT INVENTION

Figure 1A:
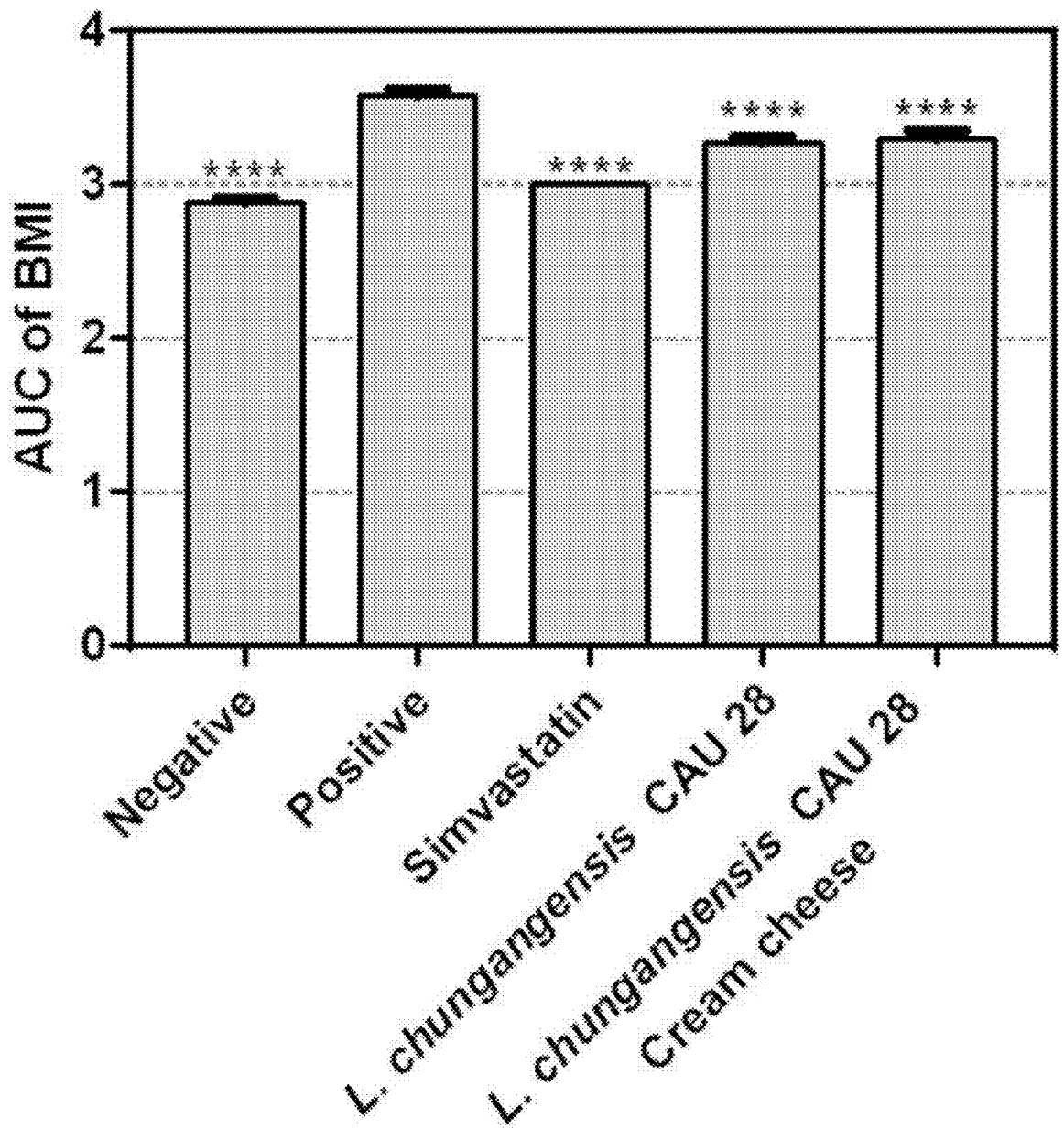
FIGS. 1a and 1b show the effect of oral administration of CAU 28 dry matter and CAU 28 cream cheese on BMI and Lee obesity index, and AUC calculated from BMI (FIG. 1a) and Lee obesity index (FIG. 1b) is displayed. Data are presented as mean±SEM (n=xx). Differences between means compared to positive controls were assessed using ANOVA. * $P<0.05$,  $P<0.005$, * $P<0.0005$, **** $P<0.0001$.

Hereinafter, the present invention will be described in detail.

However, the following examples only illustrate the present invention, and the content of the present invention is not limited to the following examples.
Experiment Method
1. Culture and Freeze-Drying of *Lactococcus chungangensis* CAU 28$^T$

*Lactococcus chungangensis* CAU 28$^T$, a kind of lactic acid bacteria, was used after being deposited in the Korean Collection for Type Cultures (KCTC; Taejon, Korea, accession number KCTC 12684BP), after inoculation in TSB (Bacto Tryptone 17 g, Bacto soytone 3 g, Glucose 2.5, Sodium chloride 5 g, Dipotassium hydrogen phosphate 2.5 g, D.W. 1000 ml) and incubated at 30° C., and was freeze-dried and made into a powder, it was dissolved in distilled water before use in the experiment.

In addition, after making a lysate of CAU28T using sterilized beads, was stored at –80° C. until used in the experiment, and was used after thawing in the experiment.
2. Production of Cream Cheese Pasteurized milk (Pasteur Milk Co., Ltd., Seoul, Korea) was heat treated at 68° C. for 30 minutes and then cooled. After the addition of 5% (v/v) *Lactococcus chungangensis* CAU 28$^T$ starter, it was cultured at 30° C. During this process, the milk acidified and a curd was formed. After heating at 70° C. and stirring for 5 minutes, whey was separated through filter paper. 0.5% salt was added to the separated curd. The finally produced cream cheese sample is freeze-dried and was stored in a dark room at 4° C. until the next experiment.
3. Experimental Animals and Breeding Conditions The mouse model used was a 6-week-old C57BL/6J mouse (n=50) model (Samtako, Osan, Korea), and C57BL/6J mice were acclimatized for 1 week prior to the experiment, and they were bred in 5 groups of 10 each. The temperature of the animal breeding room was 22° C., and the lighting was controlled for 12 hours, and these conditions were maintained for the duration of the experiment.
4. Administration and Experimental Group The experimental group was divided into 5 groups (n=10 for each group): (1) negative control, normal diet (NFD) and oral administration of PBS; (2) positive control, high-fat diet (HFD) and oral administration of PBS; (3) simvastatin group, high-fat diet (HFD) and oral administration of simvastatin; (4) *L. chungangensis* CAU 28 (CAU 28) group, high-fat diet (HFD) and oral administration of lyophilized *L. chungangensis* CAU 28; (5) CAU 28 cream cheese group, high-fat diet (HFD) and oral administration of cream cheese made with *L. chungangensis* CAU 28.

During the experimental period, the experimental group had free access to diet and drinking water. Cream cheese made from freeze-dried *L. chungangensis* CAU 28 [1×10$^8$ CFU/mouse] and *L. chungangensis* CAU 28 (1.4 g/kg/mouse) was suspended in 200 μl of sterile water and administered by oral gavage. The same volume of PBS was administered to the negative control group and the positive control group. Simvastatin (10 mg/kg) was dissolved in 200 μl of sterile water and administered orally. All mice were gavaged once a week for 12 weeks.

The weight and length of the animals were measured once a week. Fecal samples were taken and an oral glucose tolerance test (OGTT) and an insulin tolerance test (ITT) were performed a few days before the end of the study period. At the end of the 12-week treatment period, mice were sacrificed by administration of isoflurane. For further analysis, blood samples and visceral and adipose tissue were immediately harvested. All procedures and procedures were approved by Food and Drug Administration (FDA) guidelines. Animals used in this study were managed according to the principles and guidelines of the Chung-Ang University Animal Care and Use Committee (IACUC) of the Laboratory Animal Research Institute (IACUC no. 2017-00044).
5. Weight, BMI, Body Fat and Organ Weighing The body weight and body length of each mouse were measured once a week.

BMI [weight (kg)/height$^2$ (m$^2$)] was measured at 12 weeks, Lee obesity index (weight×0.33/naso-anal length) was calculated at week 1 and week 12 (Novelli et al., 2007).

Liver, lung, kidney, spleen and adipose tissue (abdominal, subcutaneous and scapular fat) were dissected; Liver, lung, kidney and adipose tissue were weighed. Organs and tissues were rinsed with saline for further analysis.

6. Glucose Tolerance Test (OGTT)

After 12 weeks of breeding, a glucose tolerance test was performed. After fasting for 16 hours, glucose (2.5 mg/g body weight, Sigma-Aldrich, St. Louis, MO, USA) was administered by oral gavage. Blood samples were taken from the tail vein at 0, 10, 20, 30, 60, 90 and 120 minutes after glucose administration. Blood glucose levels were measured using an Accu-Check Advantage blood glucose monitor (LifeScan, Johnson & Johnson, Chesterbrook, PA), the area under the curve (AUC) was calculated according to the manufacturers instructions.

7. Insulin Resistance Test (ITT)

Blood glucose changes after insulin injection were assessed by ITT. Mice were fasted for 4 h prior to intraperitoneal injection of insulin solution (0.75 UI/kg; Sigma-Aldrich, St. Louis, MO, USA). Blood samples were taken from the tail vein at 0, 10, 20, 30, 60, 90 and 120 minutes after insulin injection. Blood glucose levels were determined by an Accu-Check Advantage glucose monitor and AUC was calculated according to the manufacturers instructions.

8. Biochemical and Histological Analysis

8-1. Metabolic Parameters

Blood samples were collected after 12 weeks of treatment from two mice from each experimental group in centrifuge tubes containing EDTA. Blood was drawn by puncturing the orbit through the orbit and within the orbit. Samples were centrifuged at 1200× for 15 minutes and incubated at 4° C. for 10 minutes. Serum aspartate aminotransferase (AST), alanine aminotransferase (ALT), TC, high-density lipoprotein (HDL), low-density lipoprotein (LDL) and TG were analyzed in the serum supernatant using an appropriate assay kit (Green Cross Biopharmaceutical, Yongin, Korea). The same samples were also used for hormone measurements.

8-2. Hormone Analysis

The concentration of adiponectin in serum was measured by enzyme-linked immunosorbent assay (ELISA) using an ADP ELISA kit (CUSABIO, Houston, TX, USA) according to the method described in the kit manual. Serum leptin concentrations were measured using a Linco Human Leptin ELISA kit (Linco Research, St. Charles, MO, USA) according to the manufacturer's instructions. Sample absorbance was measured at 450 nm using an Infinite M200 NanoQuant plate reader (Tecan, Switzerland).

8-3. Cytokine Analysis

Blood samples collected after 12 weeks of treatment were used for cytokine analysis [tumor necrosis factor (TNF-α), interferon (IFN-γ), interleukin (IL) 1β and IL-6]. Blood samples were coagulated at 4° C. for 1 hour and then centrifuged at 5000× for 1 hour. The supernatant (serum) was stored at −80° C. until analysis. Cytokine concentrations were measured using an appropriate ELISA kit (R&D Systems, Minneapolis, MN, USA) according to the manufacturer's instructions. Sample absorbance was measured at 450 nm using an Infinite M200 NanoQuant plate reader (Tecan).

8-4. Flow Cytometry

Spleens were harvested from sacrificed mice and crushed on a cell strainer (SPL Life Sciences, Pocheon, Korea). Cells were counted after staining with trypan blue using a TC10 automatic cell counter (Bio-Rad, Hercules, CA, USA). It was then diluted to 2.0×10$^6$ cells/tube and stained with phycoerythrin (PE)-labeled anti-mouse antibody: CD4 or CD8 (BD Biosciences, San Jose, CA, USA) on ice for 20 min. Cells were analyzed by collecting at least 10,000 events on a FACSCalibur™ flow cytometer (BD Biosciences, San Jose, CA, USA) and BD CellQuest Pro Software (version 6.0).

8-5. Histological Analysis

Liver, abdominal, subcutaneous and scapular fats of sacrificed mice were obtained for biopsy. The intestines and adipose tissue were thoroughly washed with saline. Samples were aliquoted and fixed in 10% (v/v) neutral-buffered formalin at 0° C. for 24 h. It was then embedded in paraffin and incised at 4-5 μm to perform hematoxylin & eosin staining. The size of adipocytes in adipose tissue was measured using an optical microscope (Leica, Wetzlar, Germany).

8-6. SCFA Analysis

Mouse stool samples were collected several days prior to sacrifice. The content of SCFA (intestinal metabolite) was determined using high performance liquid chromatography (HPLC) (Dionex Ultimate 3000, Thermo Fisher Scientific, Sunnyvale, CA, USA). Samples were prepared by homogenization and centrifugation at 12,000×g at 4° C. for 20 minutes. SCFAs (acetic acid and propionic acid) were separated on an Aminex 87H column (300×10 mm, Bio-Rad). As the mobile phase (Fluke; Sigma-Aldrich), isocratic elution with 0.01 N sulfuric acid was used, and the flow rate was 0.5 ml/min. SCFAs were identified at a wavelength of 210 nm using a RefractoMax521 Refractive Index Detector (ERC, RefractoMAX520, Kawaguchi, Japan).

9. Evaluation of Anti-Obesity Effect of CAU28 Strain on 3T3-L1

9-1. Cultivation of 3T3-L1 Cell Line

The 3T3-L1 cells used in the experiment were prepared by adding FCS (Fetal Calf Serum) and Streptomycin & Penicillin antibiotics to DMEM (Dulbecco's Modified Eagle Medium) medium, and incubated at 37° C. and 5% CO$_2$ conditions. In this experiment, after seeding the 3T3-L1 cell line with FBS instead of FCS in a 12-well plate, and then cells were incubated until full in each well.

9-2. Differentiation Induction and Experimental Group

In each group, the negative control group in which 3T3-L1 cells were cultured by treating only the medium, the positive control group in which the medium containing differentiation components (Insulin, 3-Isobutyl-1-methylxanthine, Dexamethasone) was treated, and CAU 28 in the differentiation medium lysate-treated conditions were set as the experimental group. 4 days after differentiation induction, the positive control group was treated with a medium containing only Insulin. In the experimental group, lactic acid bacteria were continuously treated in the same medium condition to induce differentiation for 9 days, at this time, from the 7th day of induction of differentiation, the medium without differentiation components was treated for 2 days. The concentration of lysate was 1×10$^{10}$ CFU/ml, and 1% was treated when the cells were treated. After a total of 9 days of differentiation, the degree of adipogenesis was confirmed from the cells and the supernatant.

9-3. Oil Red O Staining from 3T3-L1

After the differentiation of 3T3-L1 cells was washed, the cells were fixed with formalin solution. After staining the adipocytes using Oil red 0 solution and observing them under a microscope, and after destaining with isopropanol, the degree of fat accumulation was confirmed through absorbance measurement.

9-4. Real-Time PCR from 3T3-L1

After the differentiation of 3T3-L1 cells was washed, RNA extraction was performed using Trizol. After RNA extraction, cDNA was synthesized. Expression levels were confirmed using Real-Time PCR using primers for fat accumulation-related factors.

9-5. Triglyceride Determination from 3T3-L1

After the differentiation of 3T3-L1 cells was removed using a scraper, the pellet obtained through centrifugation was mixed well with the solution used for triglyceride measurement, and then the cells were destroyed using sterilized beads. After centrifugation again, the supernatant was separately obtained and triglyceride was measured.

9-6. Cytokine Measurement from 3T3-L1

After 4 hours of treatment with LPS (100 ng/ml) in the positive control group and the experimental group treated with lactic acid bacteria in 3T3-L1 cells after differentiation, the supernatant was obtained and cytokines were measured.

As shown in Table 1, the Lee obesity index of all animals was compared at week 1 and week 12 in order to accurately evaluate the change in obesity of experimental animals during the entire experimental period. At week 1, there was no difference in Lee obesity index between groups (P=0.1042). However, at 12 weeks, the Lee obesity index of the positive control group was significantly higher than that of the other groups (P<0.01).

Figure 1B:
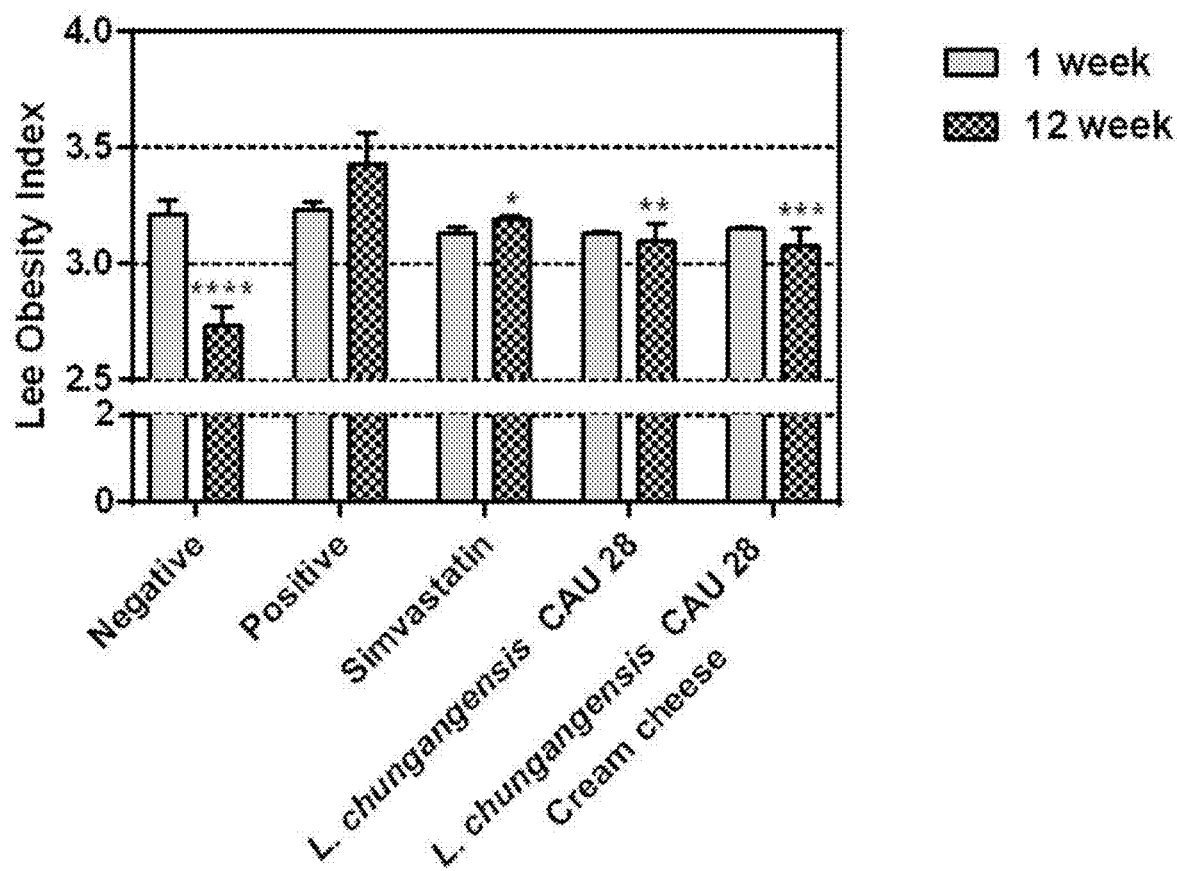

The Lee obesity index of the negative control group, CAU 28 and CAU 28 cream cheese group was significantly lower at week 12 than at week 1. The Lee obesity index of the simvastatin group was slightly higher at week 12 than at week 1 (FIG. 1b).

These results indicate that oral administration of CAU 28 dry cells and CAU 28 cream cheese suppressed obesity due to HFD, thereby reducing BMI and Lee obesity index.

TABLE 1

|  | Negative control | Positive control | Simvastatin | CAU 28 | CAU 28 CC | P-value |
|---|---|---|---|---|---|---|
| Initial body weight (g) | 23.24 ± 0.47 | 23.41 ± 0.33 | 23.73 ± 0.57 | 22.75 ± 0.35 | 23.74 ± 0.75 | 0.6456 |
| Final body weight (g) | 27.45 ± 0.73 | 41.91 ± 2.46 | 36.34 ± 3.13 | 36.47 ± 0.90 | 36.62 ± 2.72 | <0.0001 |
| AUC of BMI | 2.89 ± 0.08 | 3.57 ± 0.10 | 3.00 ± 0.00 | 3.27 ± 0.09 | 3.30 ± 0.11 | <0.0001 |
| Lee obesity index (1 w) | 3.21 ± 0.13 | 3.23 ± 0.07 | 3.13 ± 0.06 | 3.13 ± 0.03 | 3.15 ± 0.01 | 0.1042 |
| Lee obesity index (12 w) | 2.74 ± 0.17 | 3.25 ± 0.05 | 3.43 ± 0.30 | 3.09 ± 0.17 | 3.20 ± 0.19 | <0.001 |
| Lung/body weight (%) | 0.007 ± 0.001 | 0.004 ± 0.001 | 0.006 ± 0.002 | 0.005 ± 0.001 | 0.006 ± 0.001 | 0.3841 |
| Kidney/body weight (%) | 0.012 ± 0.001 | 0.009 ± 0.001 | 0.010 ± 0.002 | 0.008 ± 0.001 | 0.009 ± 0.001 | <0.01 |
| Liver/body weight (%) | 0.04 ± 0.00 | 0.032 ± 0.01 | 0.02 ± 0.00 | 0.03 ± 0.00 | 0.02 ± 0.00 | <0.0001 |
| White fat/body weight (%) | 2.10 ± 0.08 | 12.02 ± 1.44 | 5.01 ± 1.63 | 8.05 ± 0.92 | 8.45 ± 0.50 | <0.0001 |
| Brown fat/body weight (%) | 0.01 ± 0.01 | 0.036 ± 0.017 | 0.03 ±0.01 | 0.03 ± 0.01 | 0.04 ± 0.01 | <0.01 |
| TC (mg/dl) | 30.50 ± 0.50 | 72.50 ± 0.50 | 51.50 ± 1.50 | 48.50 ± 4.50 | 52.50 ± 0.50 | <0.0001 |
| TG (mg/dl) | 29.50 ± 0.50 | 40.00 ± 5.00 | 30.00 ± 5.00 | 31.50 ± 1.50 | 37.00 ± 1.00 | <0.01 |
| HDL/TC (%) | 0.98 ± 0.05 | 0.94 ± 0.00 | 1.00 ± 0.02 | 1.00 ± 0.02 | 0.99 ± 0.01 | 0.1295 |
| LDL/TC (%) | 11.50 ± 0.02 | 0.16 ± 0.01 | 0.12 ± 0.01 | 0.15 ± 0.01 | 0.13 ± 0.01 | <0.01 |
| AST (U/l) | 35.00 ± 1.00 | 61.50 ± 6.50 | 54.50 ± 2.50 | 47.50 ± 4.50 | 38.00 ± 4.00 | <0.0001 |
| ALT (U/l) | 9.50 ± 0.50 | 17.00 ± 3.00 | 10.00 ± 0.00 | 9.00 ± 0.00 | 10.00 ± 0.00 | <0.001 |

10. Statistical Analysis

Results are presented as mean±standard error (SEM). The biochemical parameter data were normally distributed and significant differences between groups were determined by one-way ANOVA using post-hoc analysis (Duncan's test). P<0.05 was considered to represent a statistically significant difference. All analyzes were performed using the GraphPad Prism statistical package (version 7.0, GraphPad Software, La Jolla, CA, USA).

Example 1: Effects of CAU 28 Dry Cells and CAU 28 Cream Cheese Intake on BMI and Lee Obesity Index There was no significant difference in the initial body weight of animals in all groups (P=0.6456; Table 1), but the AUC of BMI was clearly lower in the CAU 28, CAU 28 cream cheese, negative control and simvastatin groups compared to the positive control group (P<0.0001) (FIG. 1a).

Example 2: Effects of CAU 28 Dry Cells and CAU 28 Cream Cheese Intake on Organ and Fat Percentage Adipose tissue-to-body weight ratios for liver, lung, kidney and adipose tissue (abdominal, subcutaneous and scapular adipose tissue) were determined to investigate the effects of CAU 28 dry cells and CAU 28 cream cheese on organs and adipose tissue.

Figure 2A:
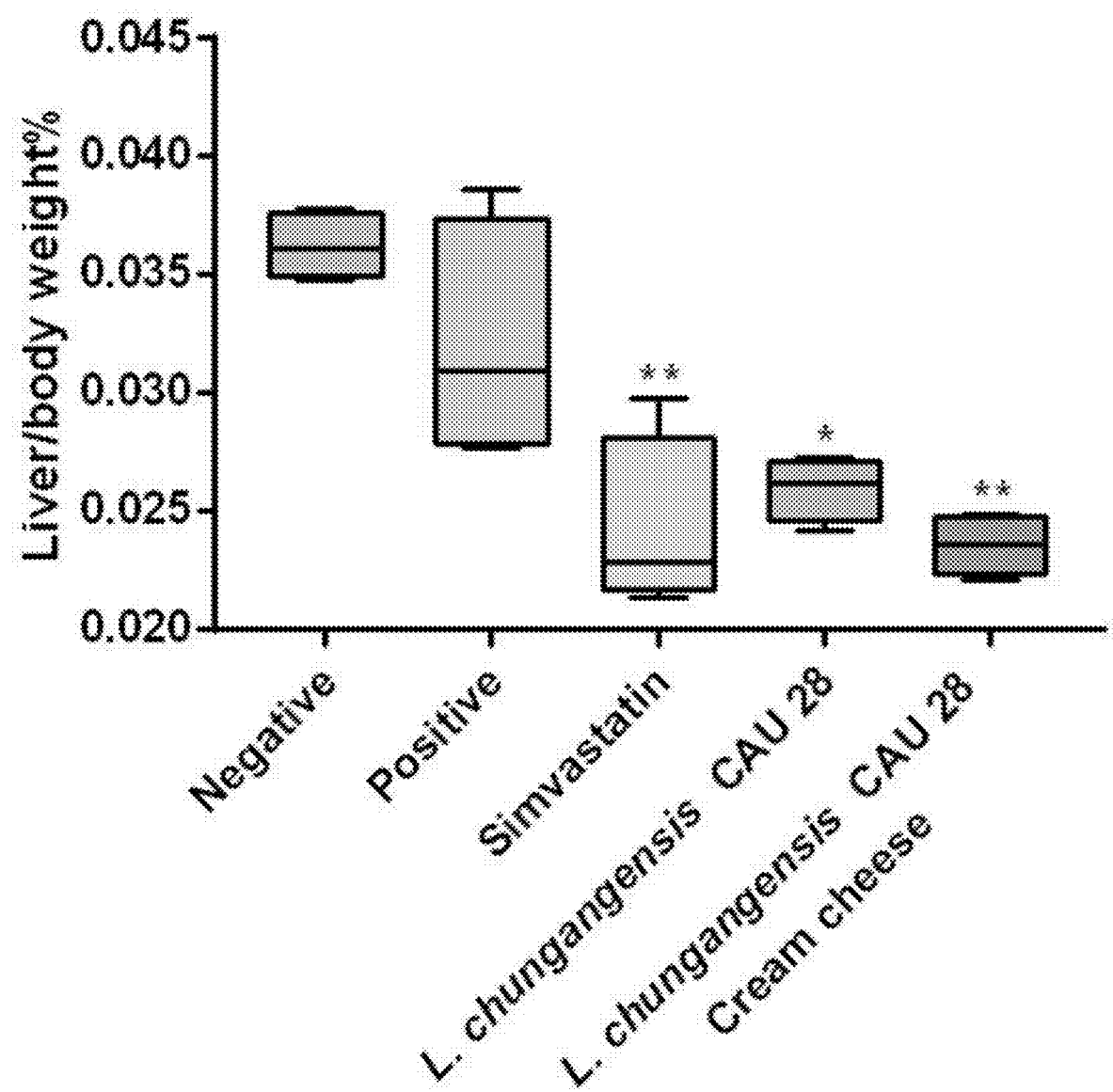
FIGS. 2a to 2e show the effect of oral administration of CAU 28 dry matter and CAU 28 cream cheese on organ and adipose tissue weight, and liver/weight ratio (FIG. 2a), lung/weight ratio (FIG. 2b), height/weight ratio (FIG. 2c), white fat/weight ratio (FIG. 2d) and brown fat/weight ratio (FIG. 2e) are shown (%). Data is denoted by xx (n=xx). Differences between means compared to positive controls were assessed using ANOVA.*$P<0.05$, $P<0.005$, *$P<0.001$, ****$P<0.0001$.

The liver/body weight of the positive control group was significantly higher than that of the CAU 28, CAU 28 cream cheese and simvastatin groups (P<0.01) (FIG. 2a). This means that oral administration of CAU 28 freeze-dried group and CAU 28 cream cheese group prevented hepatomegaly. In addition, the effect of CAU 28 cream cheese intake group was more pronounced than that of CAU 28 freeze-dried cell intake.

Figure 2B:
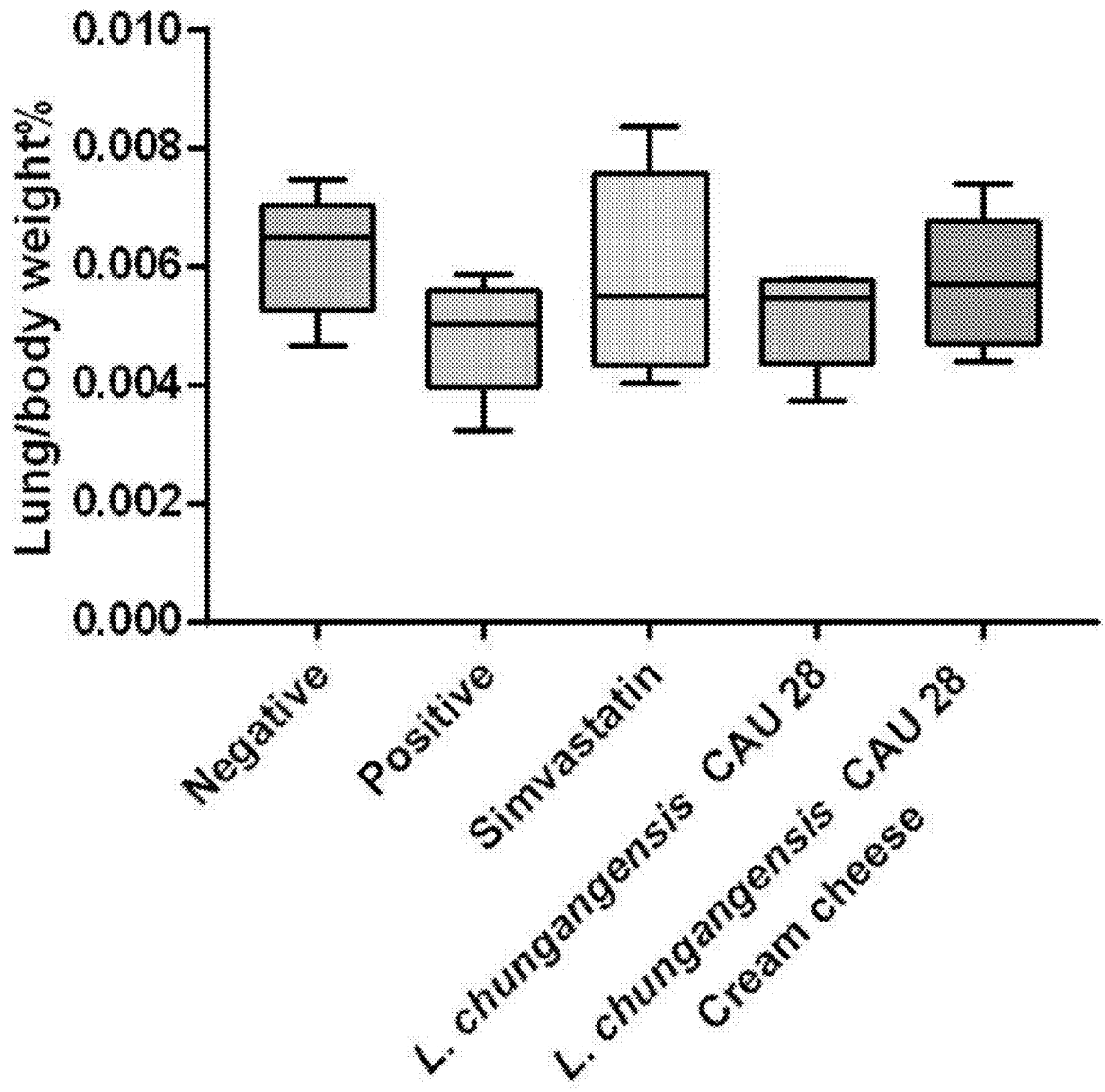
Figure 2C:
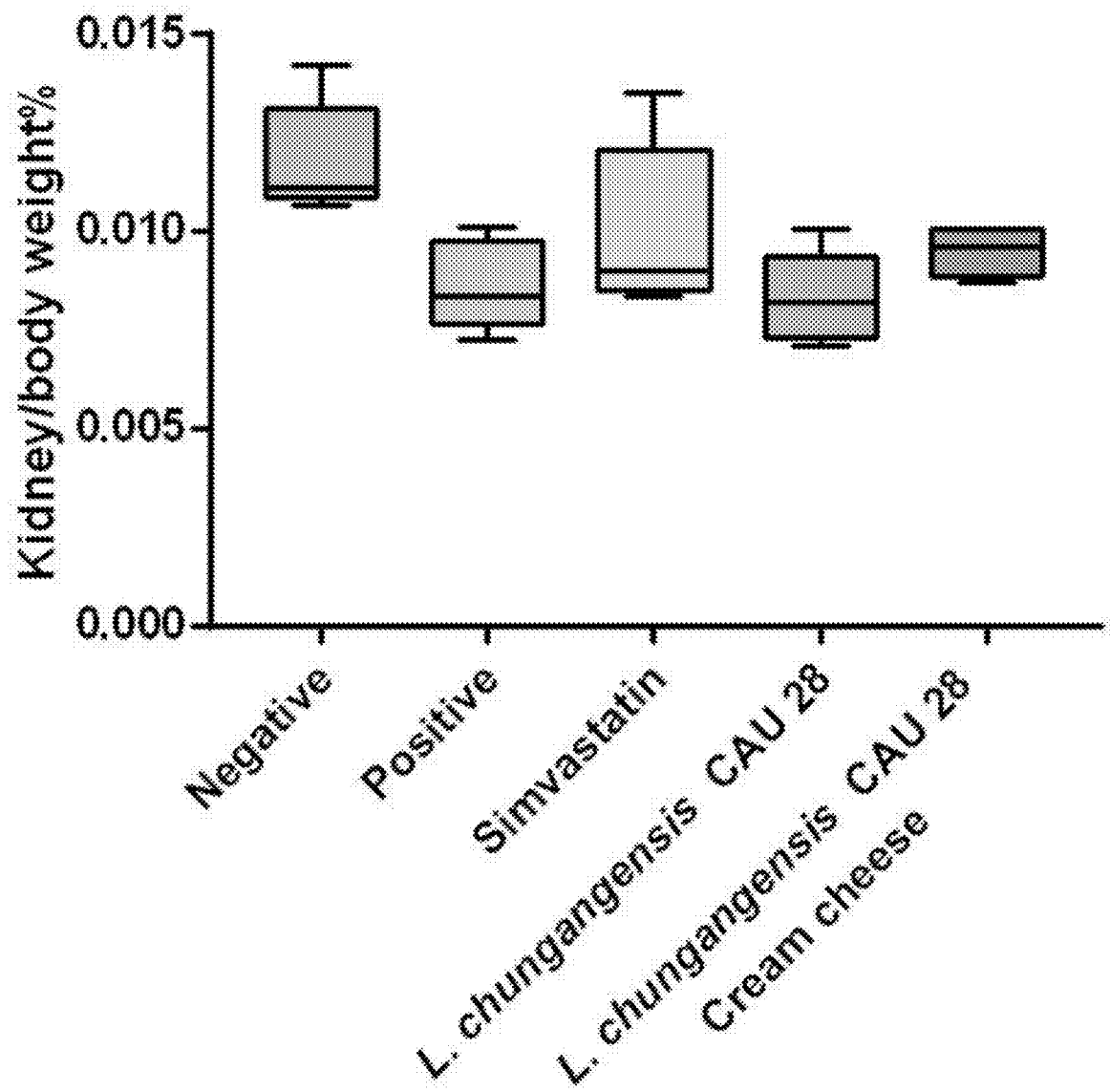

There was no significant difference in lung and height/weight ratio in the positive control group, CAU 28, CAU 28 cream cheese, and simvastatin groups (P=0.3841) (FIGS. 2b and 2c). These results suggest that the administration of CAU 28 dry cells and CAU 28 cream cheese did not damage the lungs and kidneys in HFD-induced obese mice.

Figure 2D:
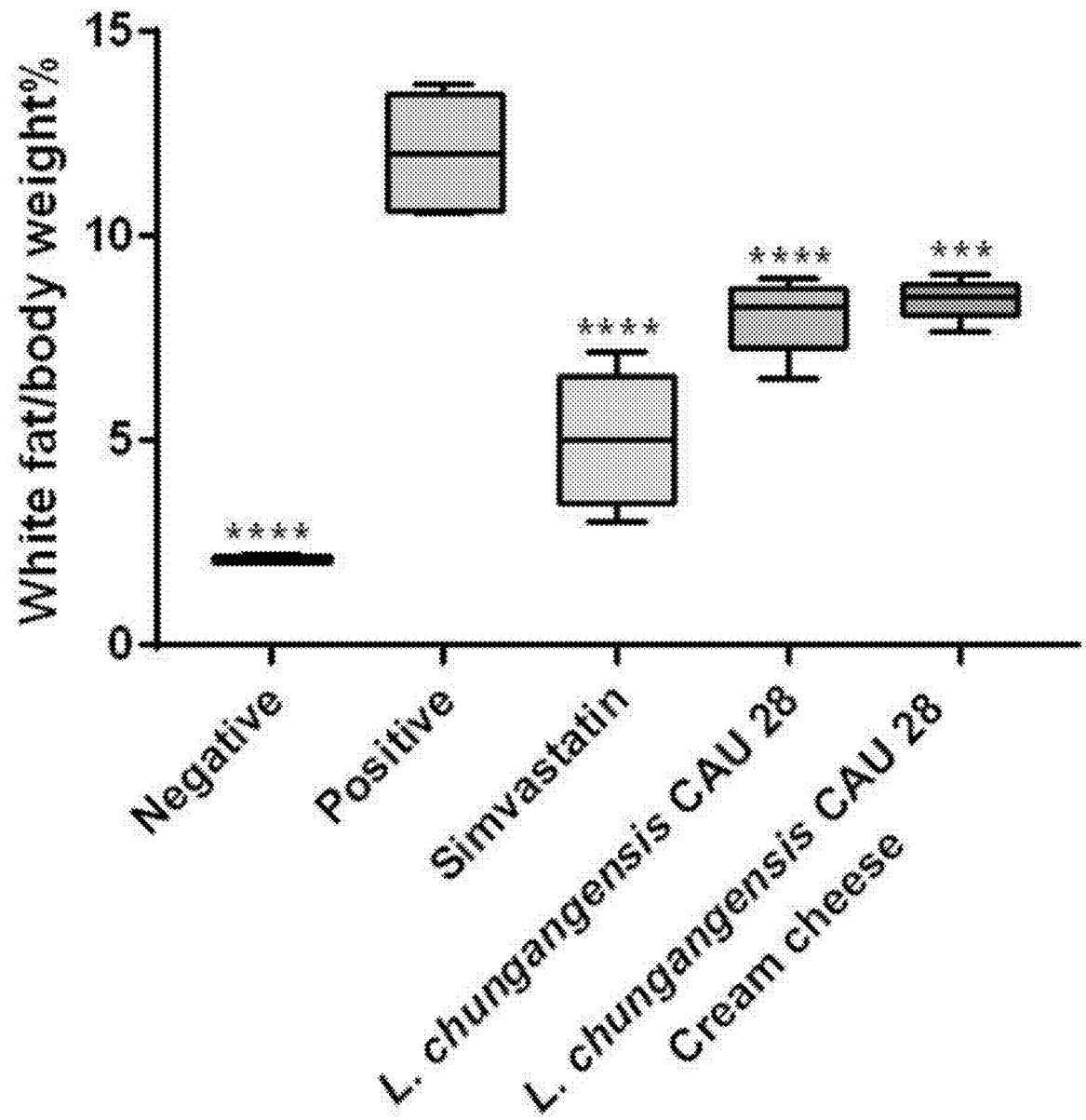

Body fat percentage is the ratio of the weight of fat to body weight and can be used to determine the degree of obesity in an animal. Abdominal and subcutaneous adipose tissue represent white fat. Scapular adipose tissue represents brown fat. The white fat/weight ratio of the positive control group was significantly higher than that of the negative control group (P<0.0001). This indicated that HFD increased the white fat/body weight ratio in obese mice. On the other hand, the white fat/weight ratio was clearly decreased in the CAU 28, CAU 28 cream cheese and simvastatin groups compared to the positive control group (P<0.0001) (FIG. 2d).

Figure 2E:
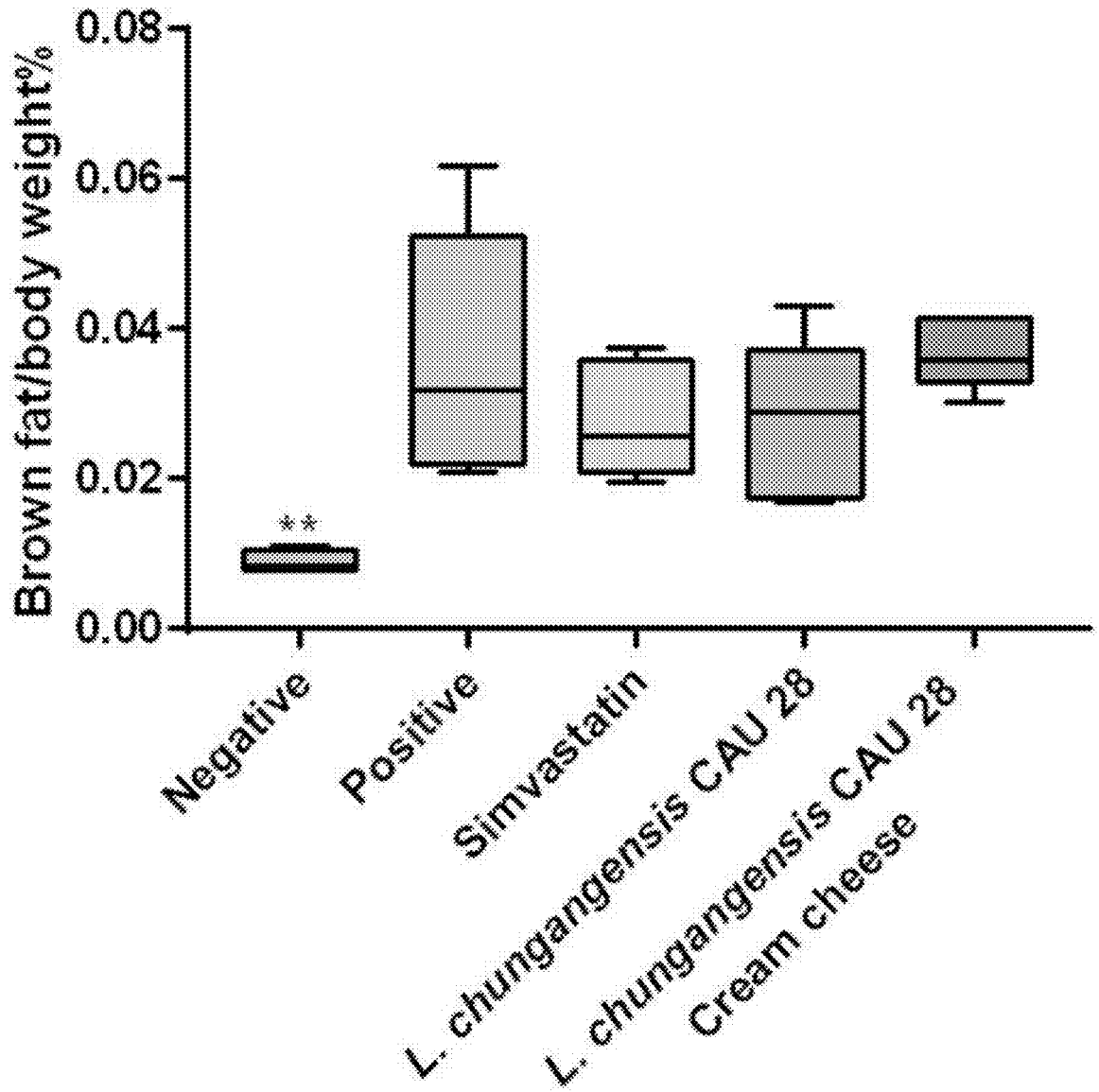

Also, the brown fat/weight ratio of the positive control group was not significantly different from the CAU 28, CAU 28 cream cheese and simvastatin groups (P=0.4594) (FIG. 2e). Therefore, oral administration of CAU 28 dry cells and CAU 28 cream cheese decreased the white fat/weight ratio while increasing the brown fat/body weight ratio in HFD-induced obese mice.

Figure 3A:
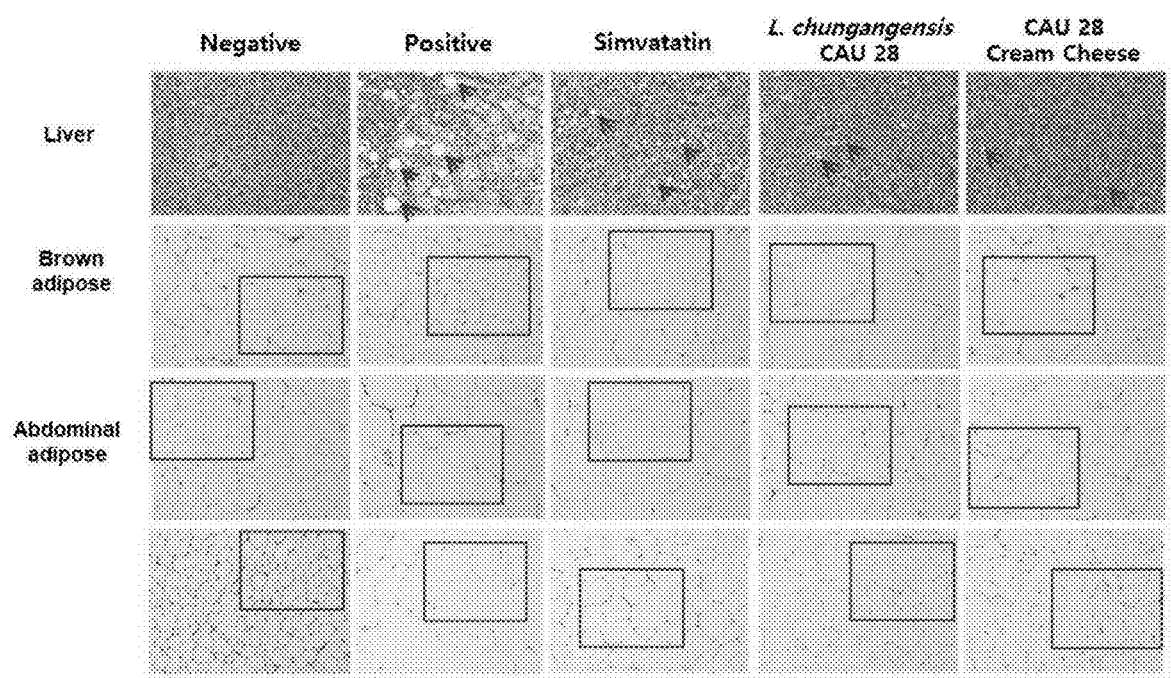
FIGS. 3a to 3d show the effect of oral administration of CAU 28 dry matter and CAU 28 cream cheese on the liver and adipose tissue, and histological analysis of liver and adipose tissue (FIG. 3a), the sizes of brown adipose tissue (FIG. 3b), abdominal adipose tissue (FIG. 3c) and subcutaneous adipose tissue (FIG. 3d) are indicated. Red arrows and squares indicate regions of interest. Differences between means compared to positive controls were assessed using ANOVA. *$P<0.05$, *$P<0.0005$, **$P<0.0001$.

Example 3: Effects of CAU 28 Dry Cells and CAU 28 Cream Cheese Intake on Hepatic Steatosis and Adipocyte Size As a result of histological analysis, it was confirmed that lipid accumulation was abnormal in the liver of the positive control group (FIG. 3a). In the positive control group, vesicle damage was observed in the liver tissue, the fat content of the liver was high, and cell contents leak, the cells swell and the cell membranes are destroyed as a large amount of fat accumulated in the blood vessels. On the other hand, as a result of oral administration of CAU 28 dry cells and CAU 28 cream cheese to HFD-induced obese mice, hepatic steatosis was less than that of the positive control group, hepatocytes had fewer fat vacuoles, morphologically, it was similar to that of the negative control group. Hepatic fat droplets in the simvastatin group were smaller than in the positive control group, but the number did not decrease significantly in the simvastatin group.

Hypertrophy of adipocytes in abdominal and subcutaneous fat was more pronounced in the positive control group and the simvastatin group than in the CAU 28 and CAU 28 cream cheese groups, but the brown adipocytes were the opposite. These results indicate that ingestion of CAU 28 dry cells and CAU 28 cream cheese suppressed the accumulation of lipids in hepatocytes and adipocytes. That is, the effects of CAU 28 dry cells and CAU 28 cream cheese were more pronounced than the effects of simvastatin and reduced the degree of liver damage in the HFD-induced obese group.

Figure 3B:
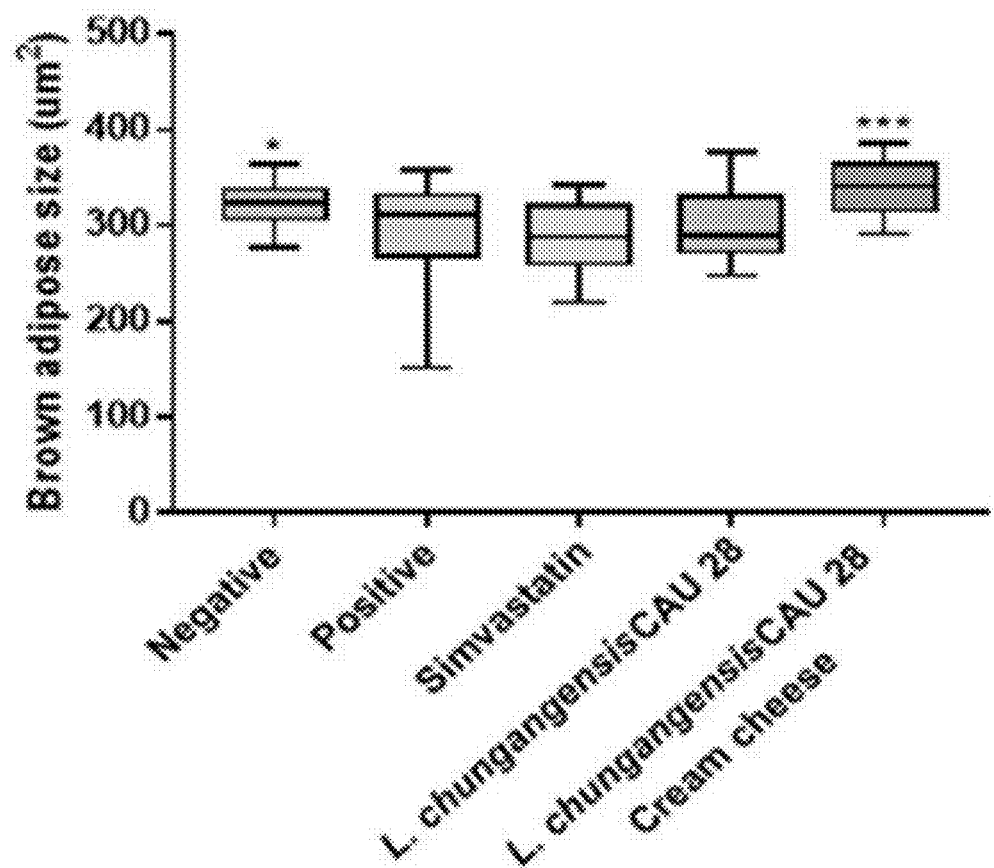
Figure 3C:
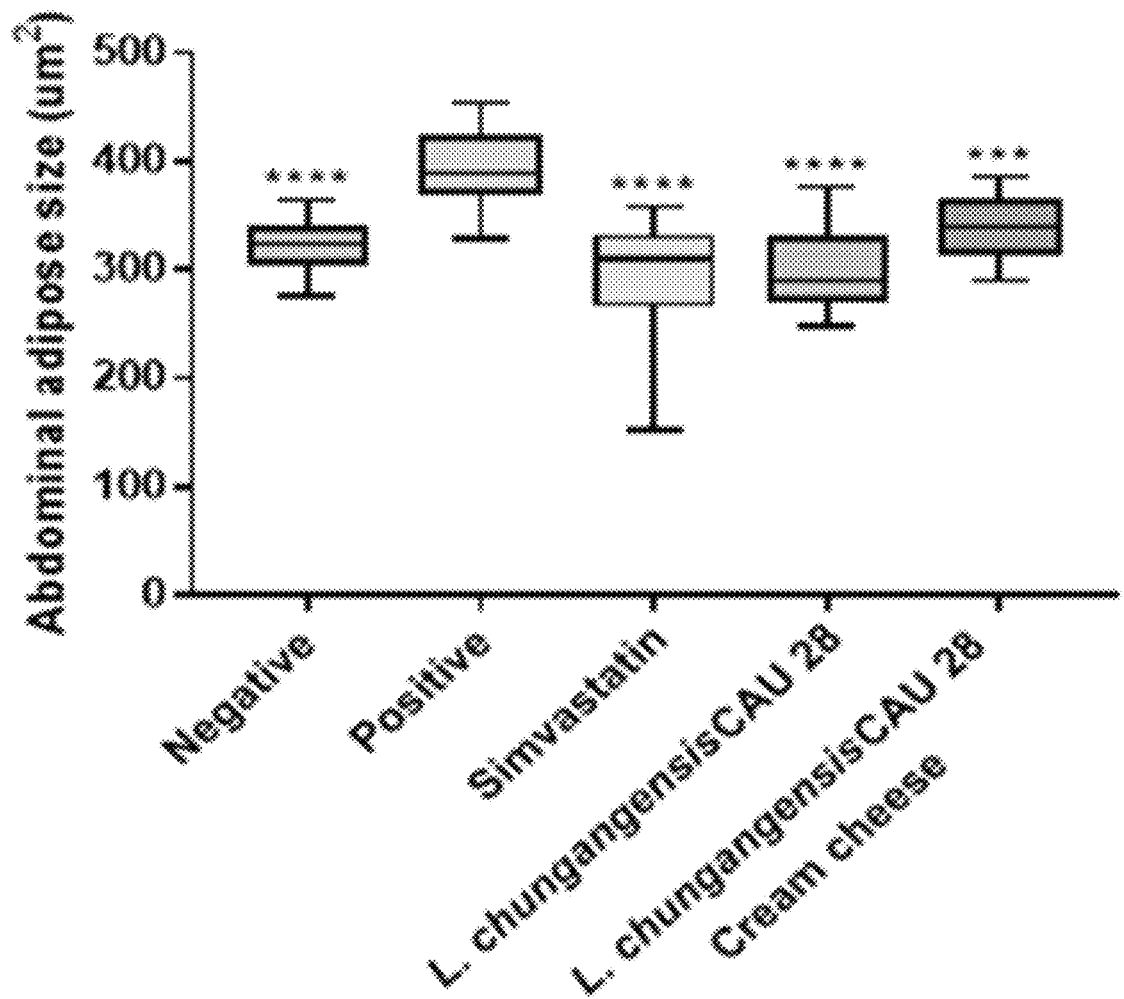
Figure 3D:
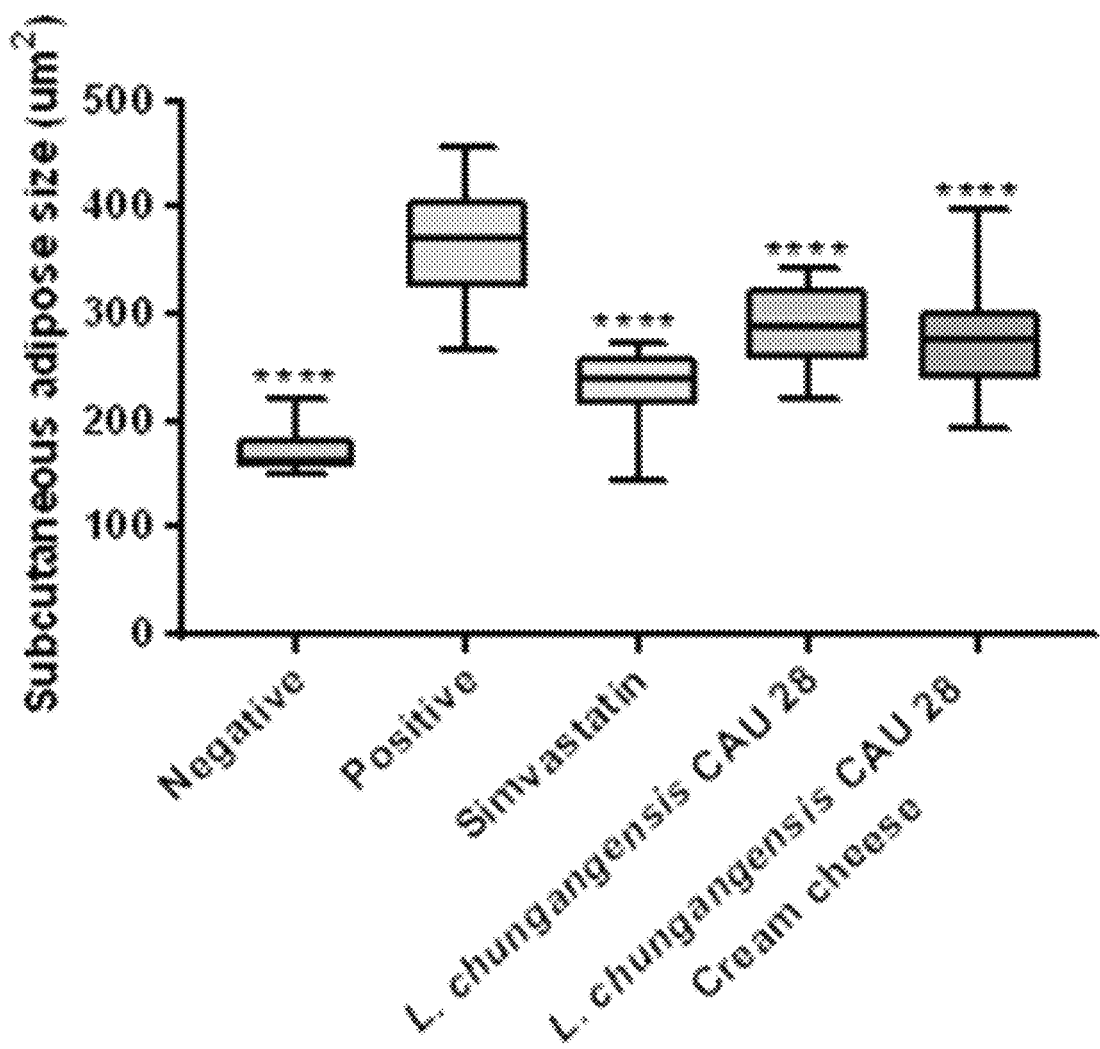

As shown in FIG. 3b, the size of the brown and white adipose tissue (abdominal and subcutaneous) of the mouse was measured. The brown adipose tissue of the positive control group was smaller than that of the CAU 28 cream cheese group (P<0.001) and the negative control group (P<0.05). However, there was no difference in size between the CAU 28 dry cells and the positive control (P=0.9167) (FIG. 3b). Abdominal and subcutaneous adipose tissue were significantly smaller in all other groups than the positive control group (P<0.001) (FIGS. 3c and 3d).

Figure 4A:
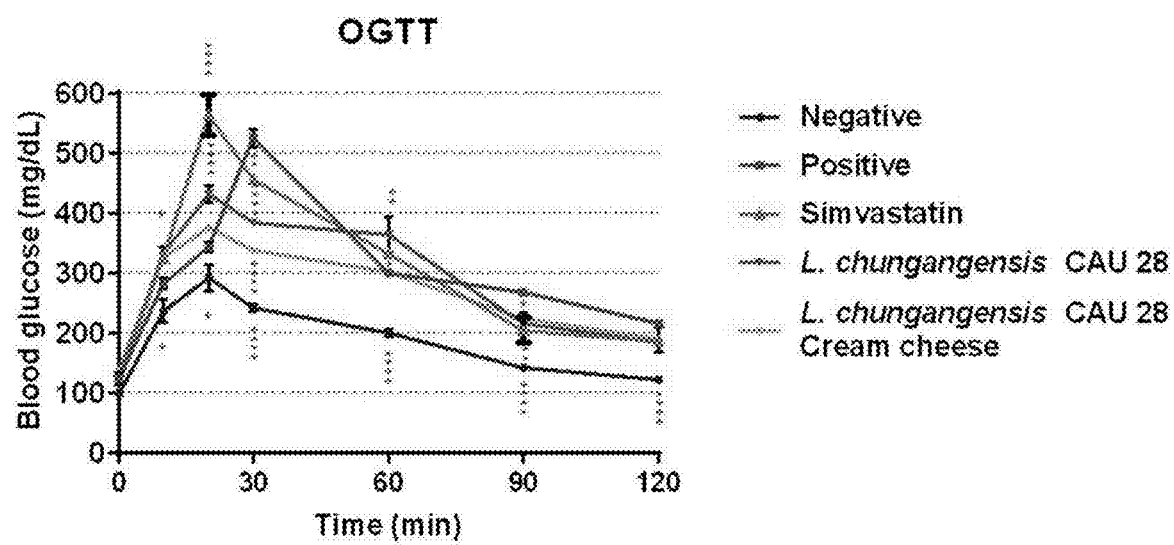
FIGS. 4a and 4b show the effect of oral administration of CAU 28 dry matter and CAU 28 cream cheese on OGTT.

Example 4: Effects of CAU 28 Dry Cells and CAU 28 Cream Cheese Intake on OGTT OGTT was used to determine the glycemic response to surgically administered glucose in all groups of animals after 12 weeks. In all groups, the blood glucose concentration increased immediately after glucose administration and reached the highest concentration 20-30 minutes after glucose administration. (FIG. 4a). The peak blood glucose concentration of the CAU 28 and CAU 28 cream cheese groups was lower than that of the positive control group and the simvastatin group.

Figure 4B:
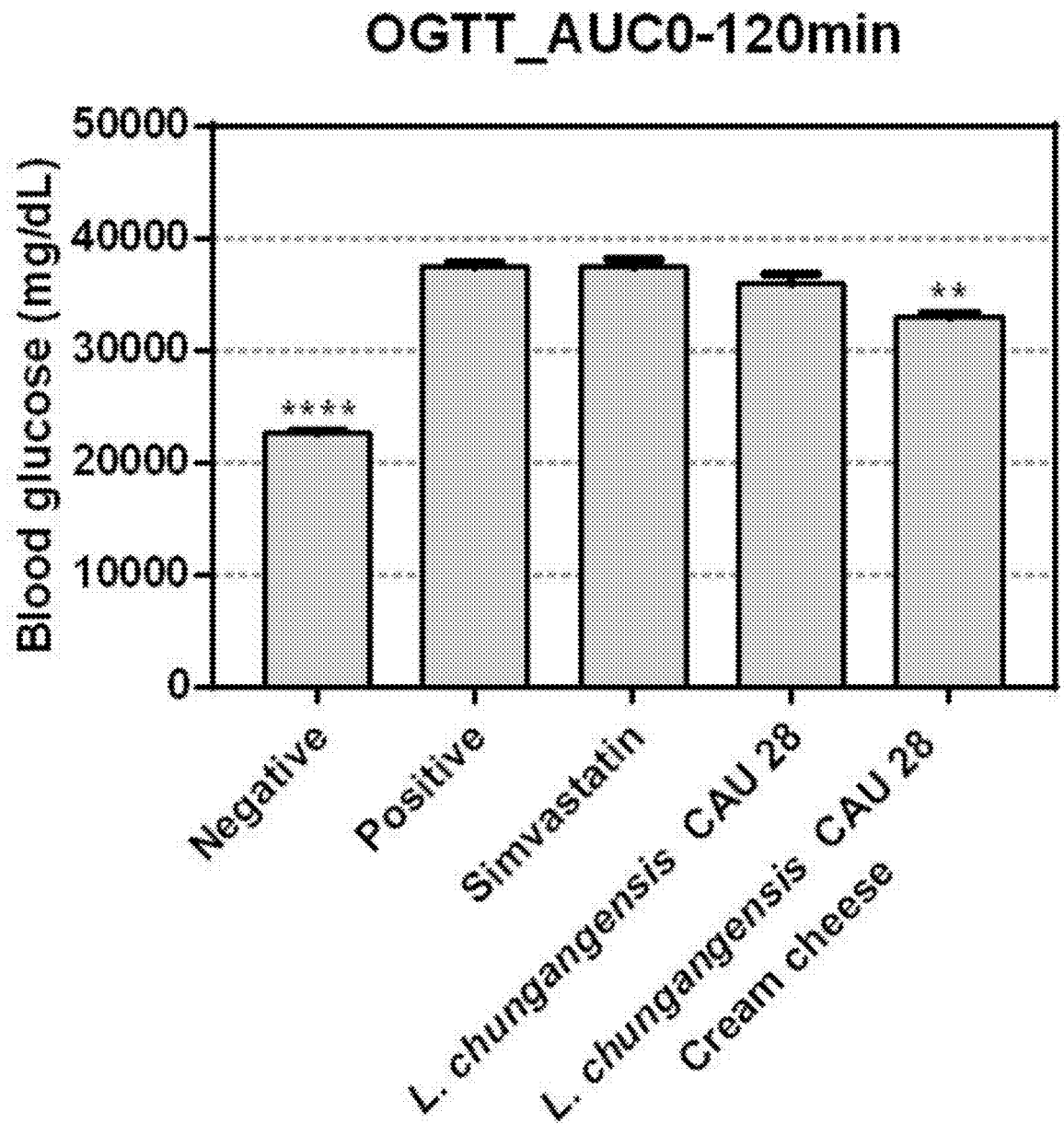

The blood glucose concentration in all groups decreased immediately after reaching the peak level, but the blood glucose concentration AUC in CAU 28 cream cheese and the negative control group was significantly lower than that in the positive control group (P<0.01), there was no significant difference between the blood glucose concentrations of CAU 28, simvastatin and positive control (P=0.2082) (FIG. 4b).

These results suggest that the intake of CAU 28 dry cells and CAU 28 cream cheese reduced the blood glucose concentration in HFD-induced obese mice.

Figure 5A:
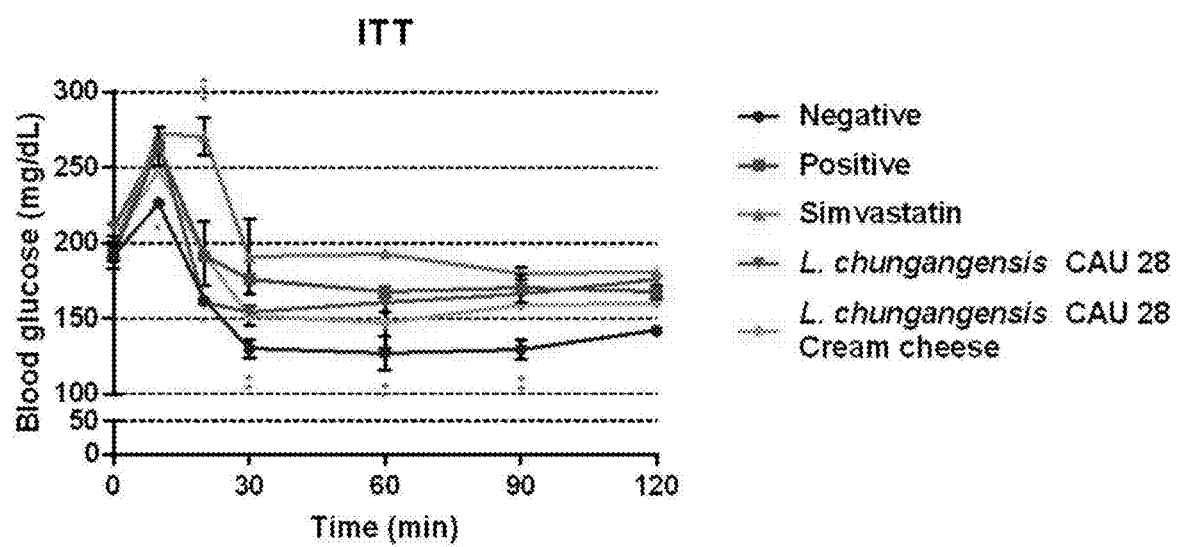
FIGS. 5a and 5b show the effect of oral administration of *L. chungangensis* CAU 28 and CAU 28 cream cheese on ITT.

Example 5: Effects of CAU 28 Dry Cells and CAU 28 Cream Cheese Intake on ITT To evaluate the insulin resistance of mice in each group, blood glucose changes were measured by short-term ITT after insulin injection. Blood glucose concentration increased immediately after insulin injection in all groups, and the peak reached 20 minutes after insulin injection (FIG. 5a). Thereafter, the blood glucose concentration immediately decreased and reached a new low level 30 minutes after the insulin injection, which was maintained until the end of the measurement (120 minutes). The blood glucose concentration in the simvastatin group was significantly higher than that in the positive control group (P<0.01). However, the blood glucose concentration of CAU 28, CAU 28 cream cheese and the negative control group was lower than that of the positive control group (FIG. 5b).

Figure 5B:
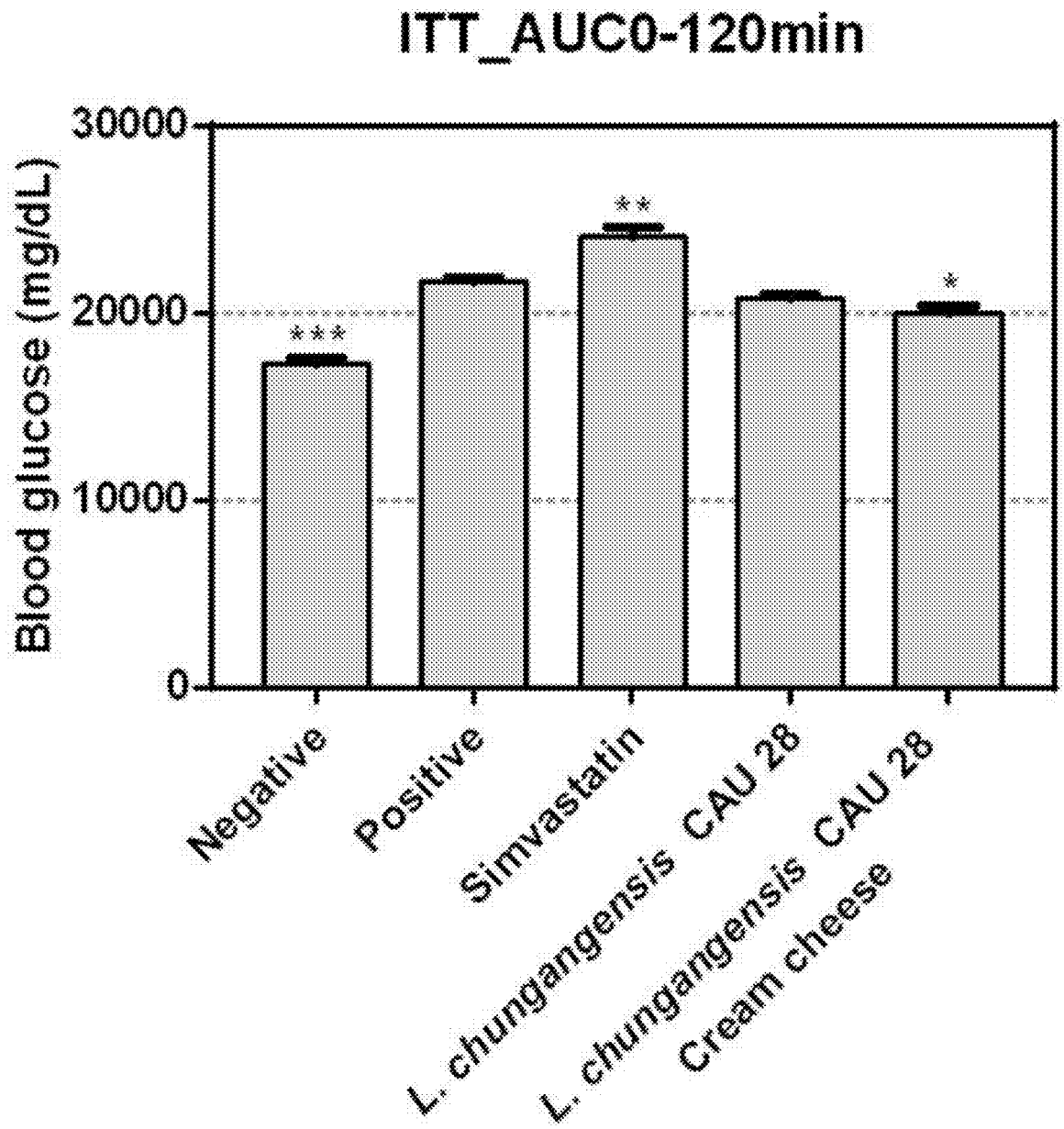

In addition, there was a significant difference only in the AUC values of the CAU 28 cream cheese group, the negative control group and the positive control group (P<0.05) (FIG. 5b).

These results indicated that ingestion of CAU 28 dry cells and CAU 28 cream cheese reduced blood glucose concentration in ITT.

Example 6: Effect of CAU 28 Dry Cells and CAU 28 Cream Cheese Intake on Blood Inflammatory Markers To investigate the effect of CAU 28 dry cells and CAU 28 cream cheese intake on cytokine and chemokine production, cytokine and chemokine concentrations in the serum of animals in each group were investigated.

Figure 6A:
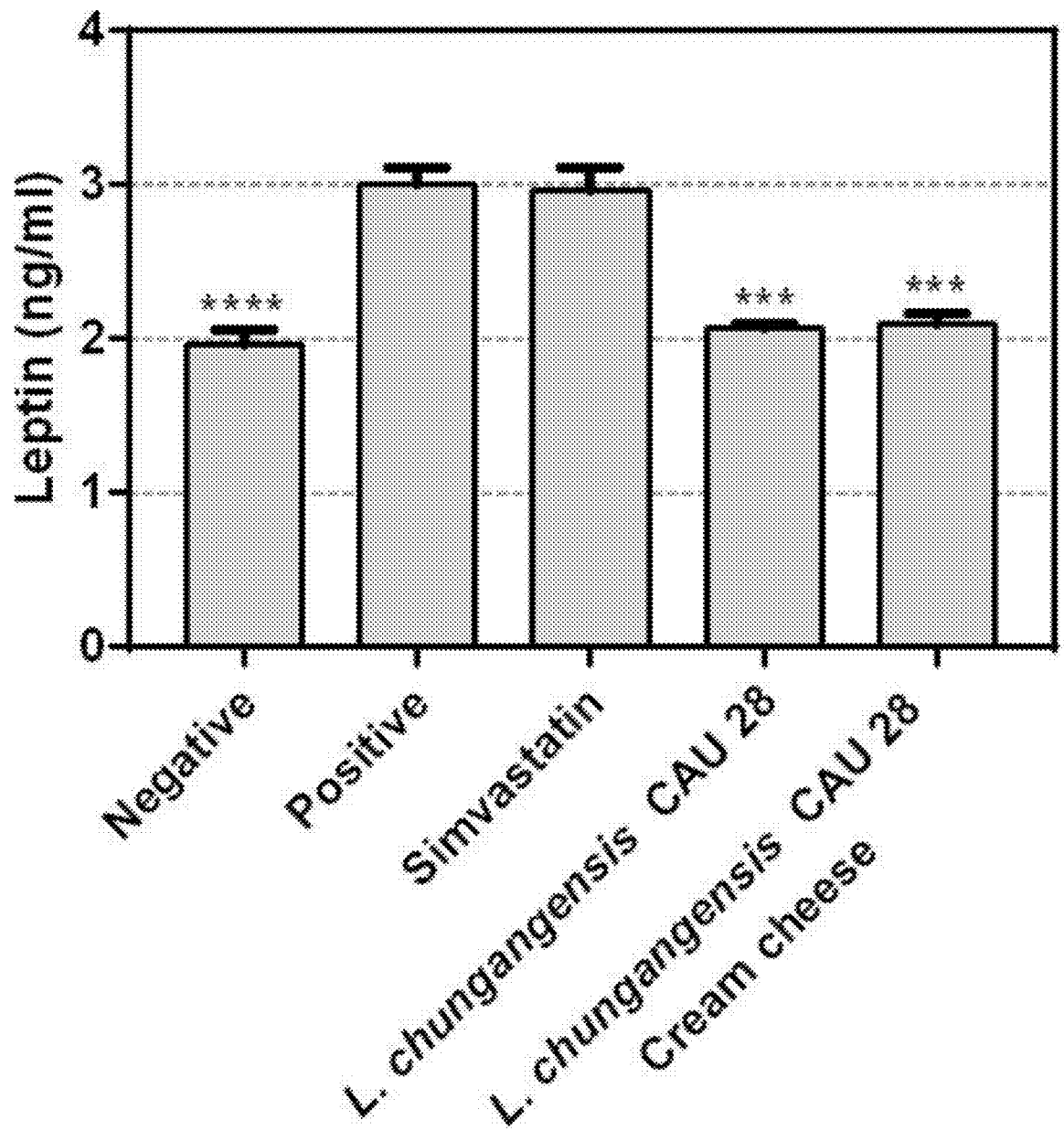
FIGS. 6a to 6f show the effect of oral administration of CAU 28 dry matter and CAU 28 cream cheese on adipokine and serum cytokine levels, and are the results of measuring each protein level using ELISA.

Serum leptin levels in the positive control group were significantly higher than those in the negative control group (P<0.0001), and this indicates that HFD induces leptin resistance (FIG. 6a). The serum leptin concentration of the CAU 28 and CAU 28 cream cheese groups was significantly lower than that of the positive control group (P<0.0001). There was no statistically significant difference in serum leptin concentrations between the simvastatin group and the positive control group (P=0.9971). These results indicate that oral administration of CAU 28 dry cells and CAU 28 cream cheese reduced serum leptin levels in HFD-induced obese mice.

Figure 6B:
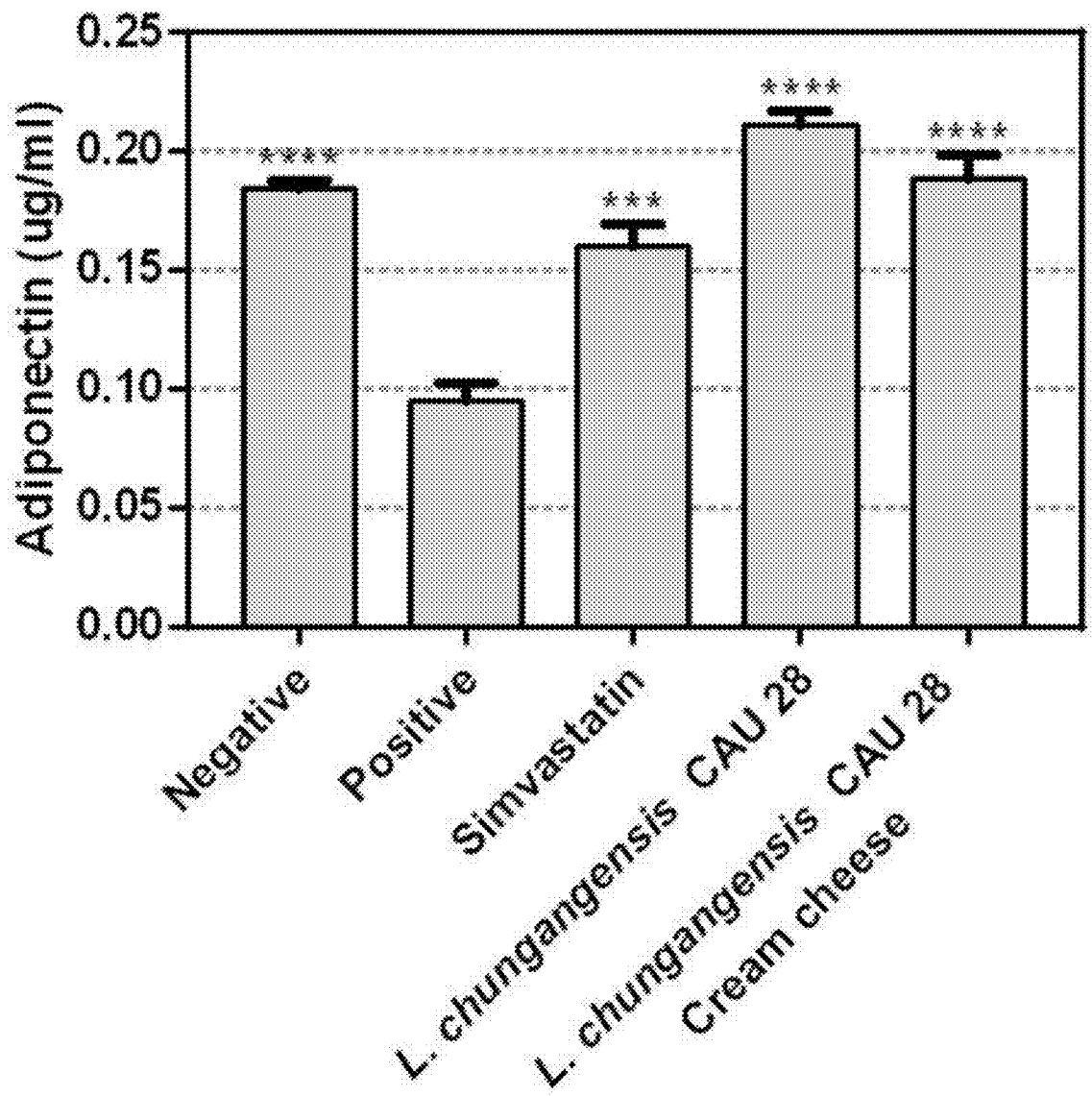
Figure 6C:
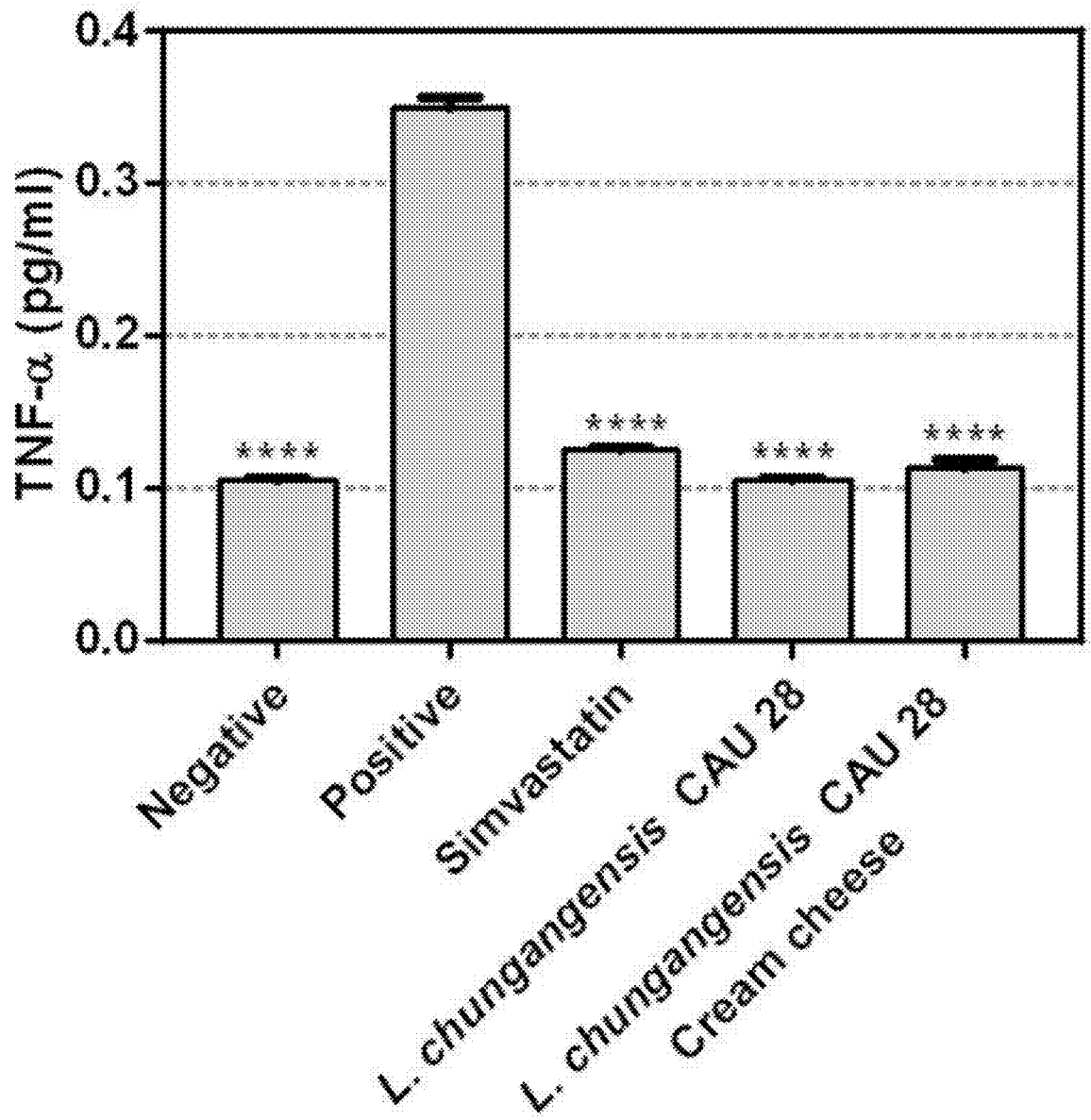
Figure 6D:
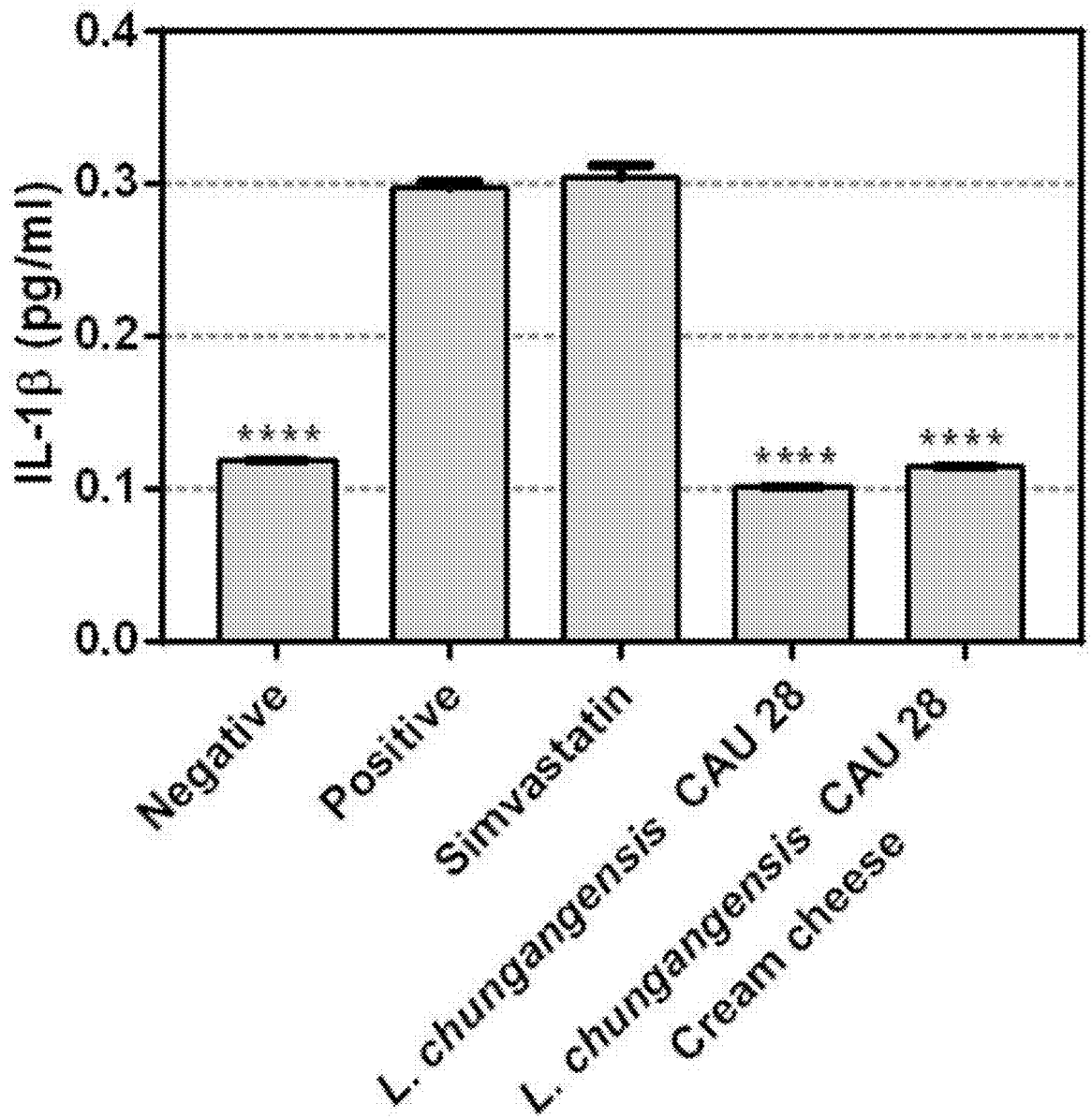
Figure 6E:
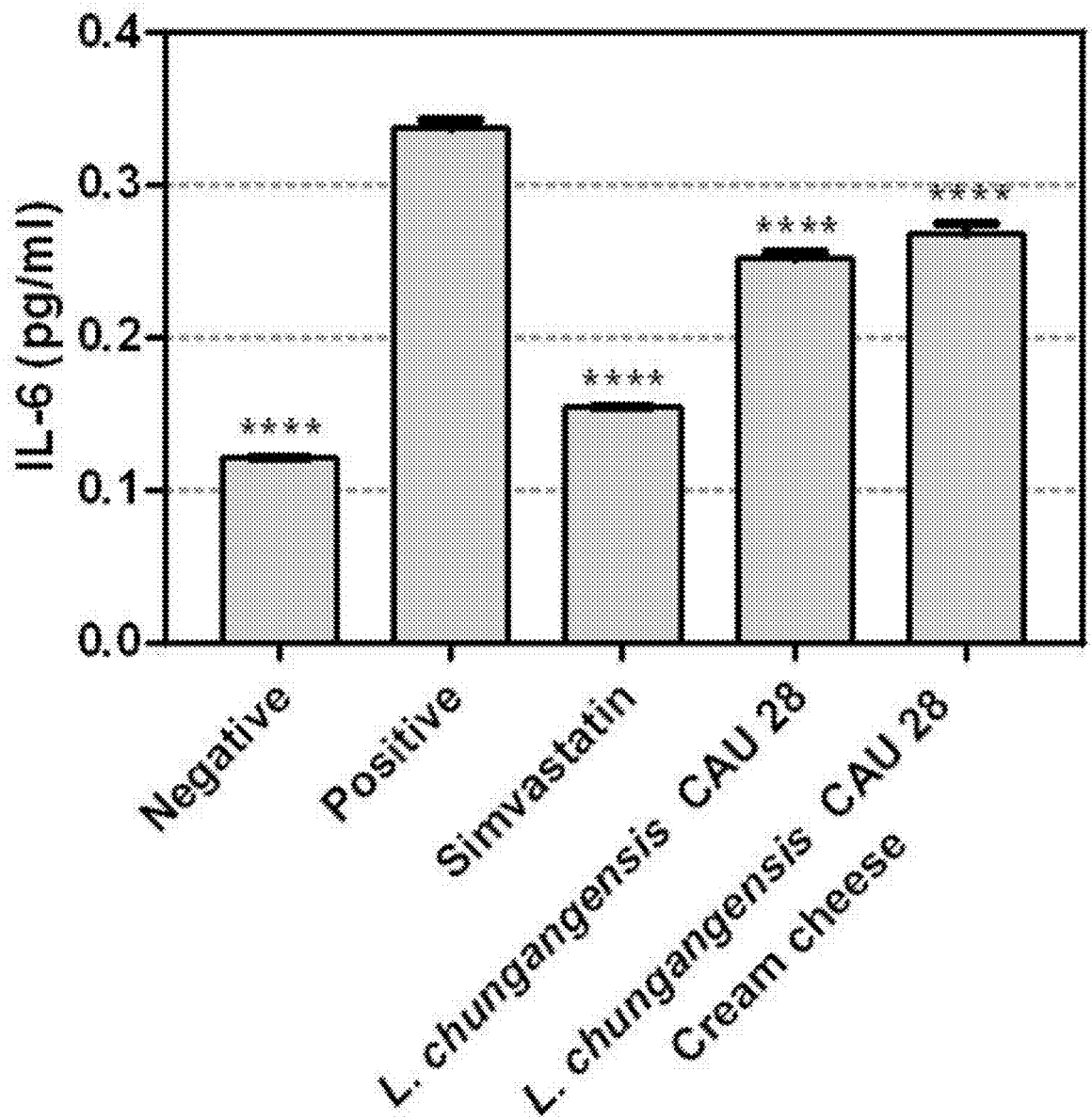
Figure 6F:
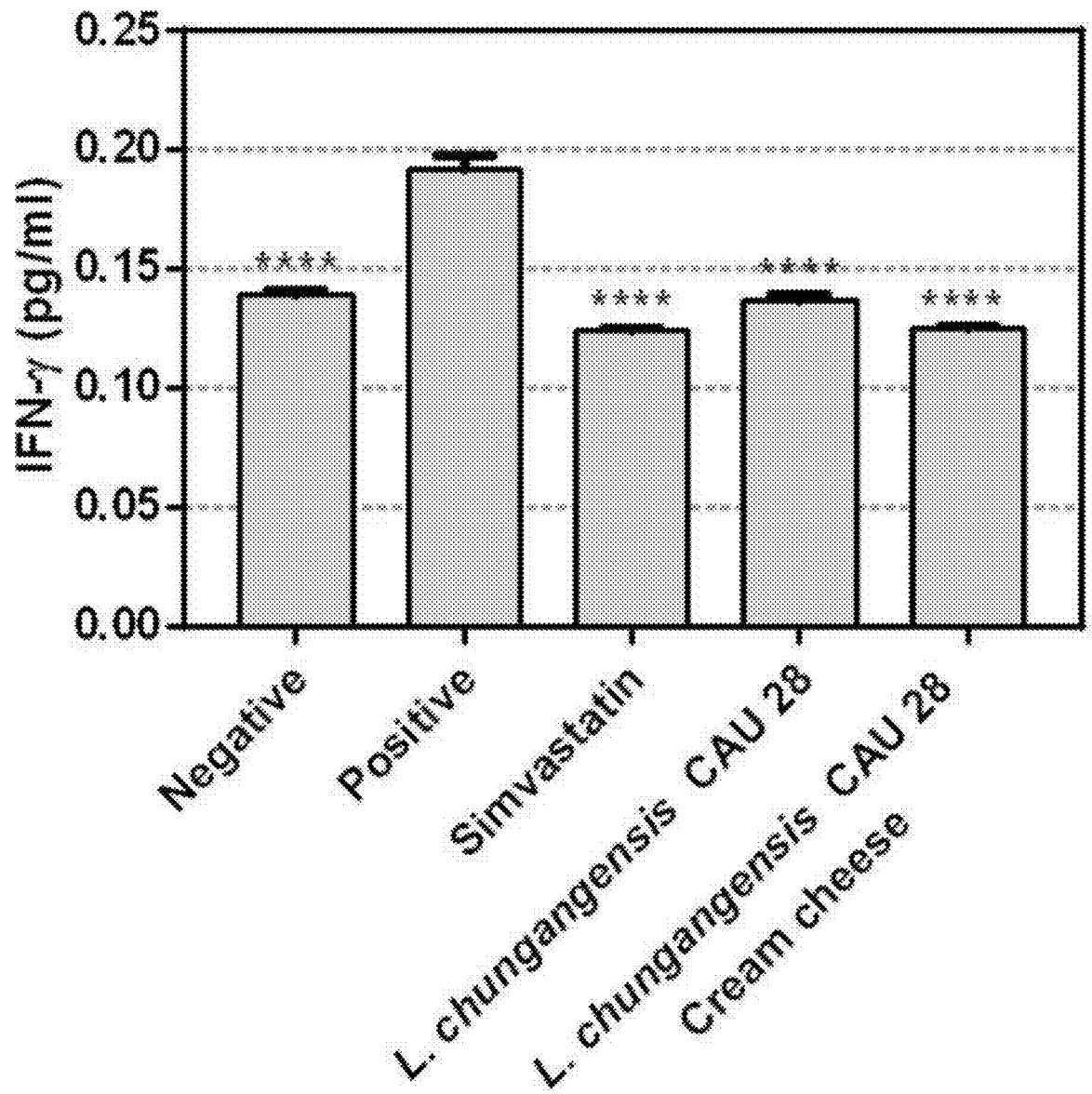

Serum adiponectin levels were clearly higher in the negative control group than in the positive control group (FIG. 6b). It is known that increased oxidative stress decreases adiponectin secretion, and adiponectin is mainly secreted from adipocytes and is known to play a role in improving hyperlipidemia by increasing insulin sensitivity and reducing sugar production in the liver. That is, it was shown that a high-fat diet resulted in a decrease in adiponectin levels in HFD-induced obese mice, but serum adiponectin levels in the CAU 28 and CAU 28 cream cheese groups (P<0.0001) and in the simvastatin group (P<0.001) were significantly higher than in the positive control group.

Therefore, these results indicate that oral administration of CAU 28 dry cells and CAU 28 cream cheese increases serum adiponectin levels in HFD-induced obese mice.

When fat accumulates in the body, NADPH (nicotinamide adenine dinucleotide phosphate) oxidase is activated and systemic oxidative stress is increased. Increased oxidative stress is known to increase inflammatory cytokines TNF-α (tumor necrosis factor-alpha), MCP-1 (monocyte chemotactic protein-1), IL-6 (interleukin-6), and the like. Serum concentrations of TNF-α, IL-β, IFN-γ, and IL-6 were significantly higher in the positive control group than in the negative control group, CAU 28, and CAU 28 cream cheese group (P<0.0001) (FIG. 6c-f). TNF-α, IL-β, IFN-γ, and IL-6 are inflammatory cytokines. Therefore, these data suggest that oral administration of CAU 28 dry cells and CAU 28 cream cheese can reduce or inhibit oxidative stress by reducing the level of pro-inflammatory cytokines in HFD-induced obese mice.

Example 7: Effects of CAU 28 Dry Cells and CAU 28 Cream Cheese Intake on Lymphocytes To investigate the effect of HFD on the immune system of HFD-induced obese mice, the number of T lymphocytes in the spleen was measured (FIGS. 7a and 7b).

Figure 7A:
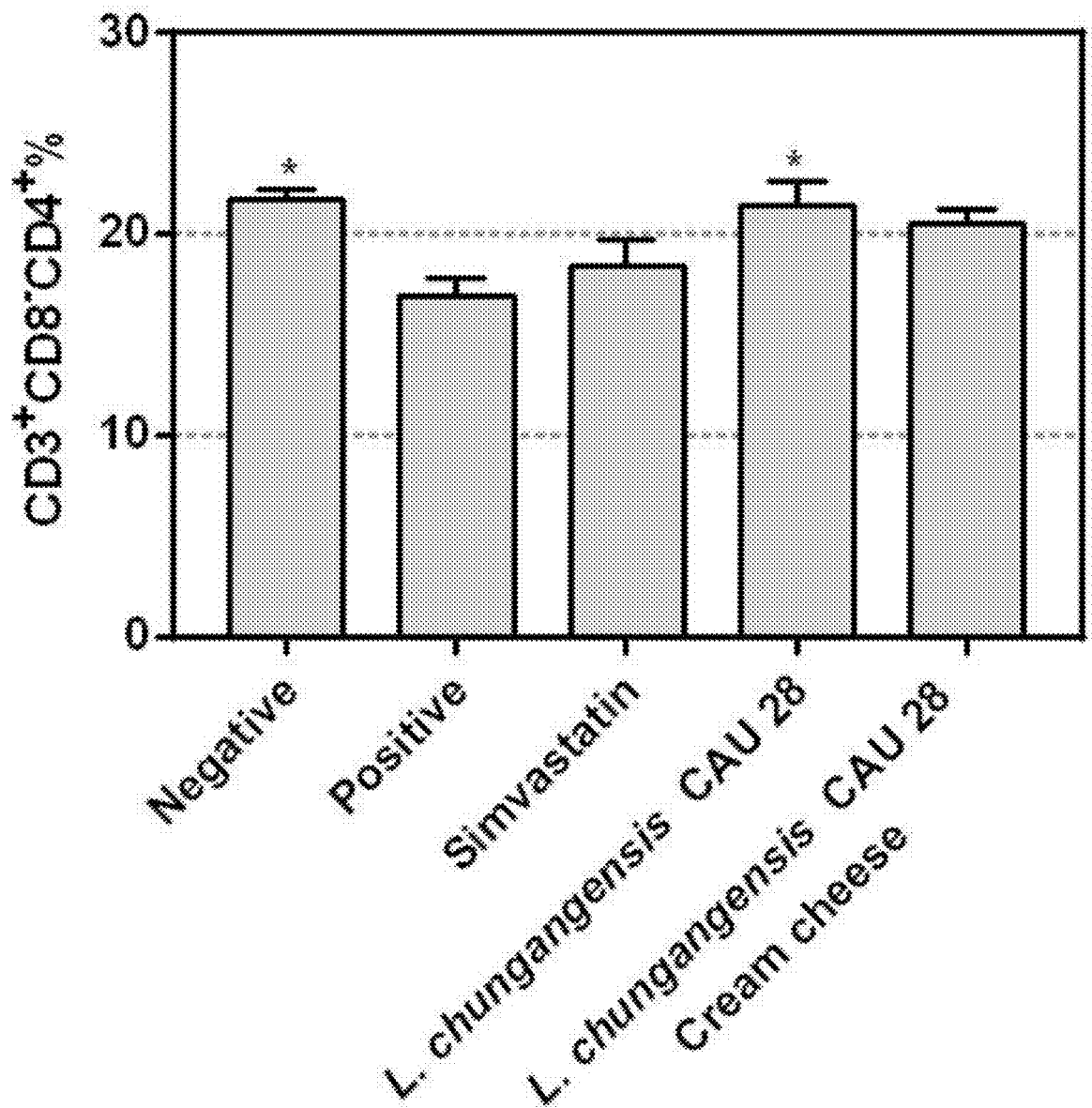
FIGS. 7a and 7b show the effect of oral administration of CAU 28 dry matter and CAU 28 cream cheese on T cell activation, T cell activation was assessed using flow cytometry. The percentages of helper T cells (CD3$^+$ CD4$^+$ CD8$^-$) (FIG. 7a) and cytotoxic T cells (CD3$^+$ CD4$^-$ CD8$^+$) (FIG. 7b) are indicated. Differences between means compared to positive controls were assessed using ANOVA. *P<0.05, **P<0.005.
Figure 7B:
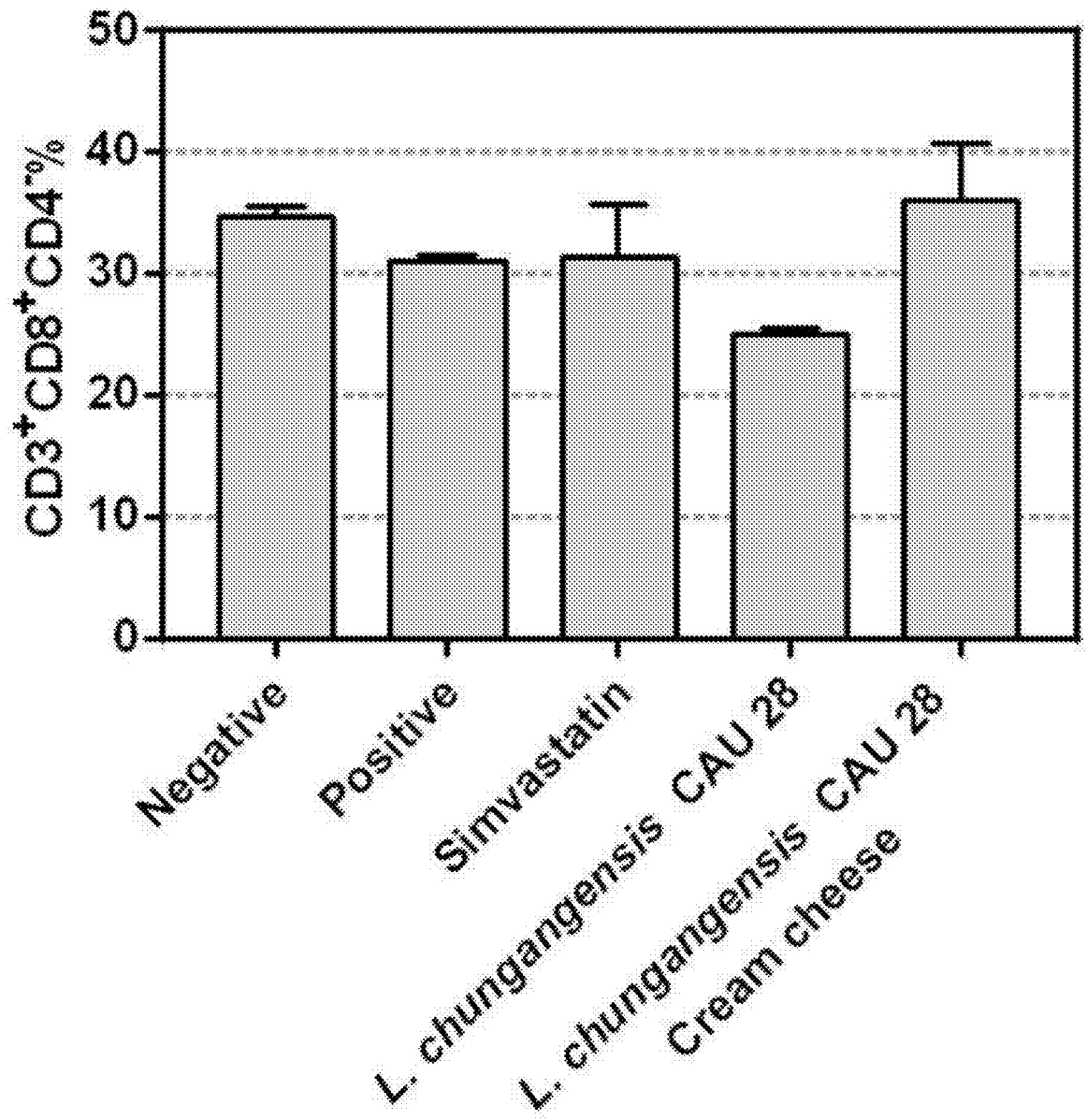

The number of CD4$^+$ T cells was significantly lower in the positive control group than in the negative control group (P<0.05) (FIG. 7a). This indicates that HFD reduced CD4$^+$ T cell counts in obese mice. As a result of the measurement, the number of CD4$^+$ T cells in the CAU 28 and CAU 28 cream cheese groups was higher than that of the positive control group.

The number of CD8$^+$ T cells in the negative control group and the CAU 28 cream cheese group was higher than that in the positive control group, but the CD8$^+$ T cell number in the CAU 28 group was lower than that in the positive control group. (FIG. 7b).

Therefore, oral administration of CAU 28 dry cells and CAU 28 cream cheese was shown to enhance the immune response by increasing the number of CD4$^+$ helper T cells.

Figure 8A:
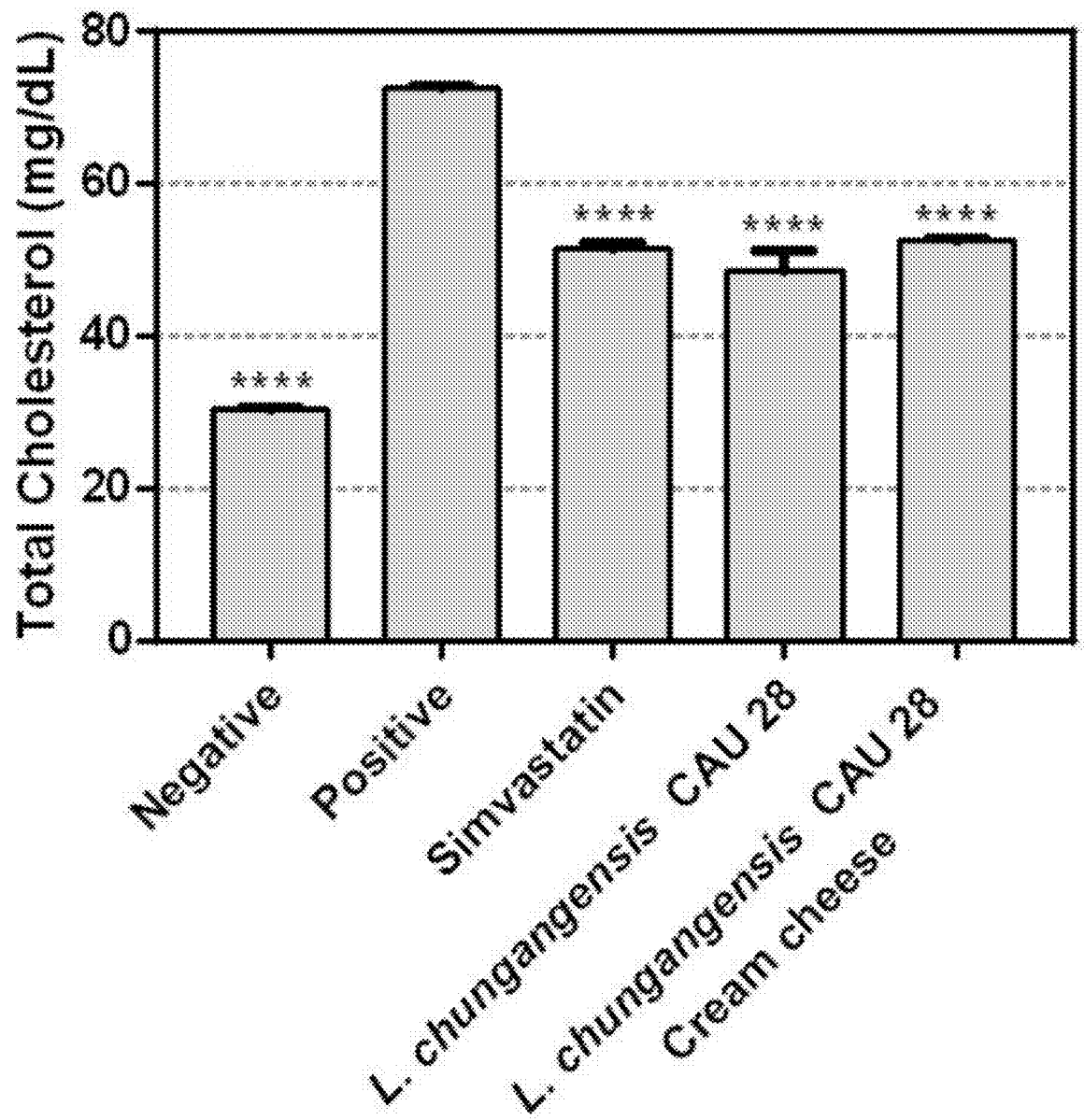
FIGS. 8a to 8d show the effect of oral administration of CAU 28 dry matter and CAU 28 cream cheese on blood lipids, serum TC (FIG. 8a), HDL/TC (FIG. 8b), LDL/TC (FIG. 8b) and TG (FIG. 8d) values are shown. Differences between means compared to positive controls were assessed using ANOVA. P<0.005, *P<0.0005, ****P<0.0001.
Figure 8B:
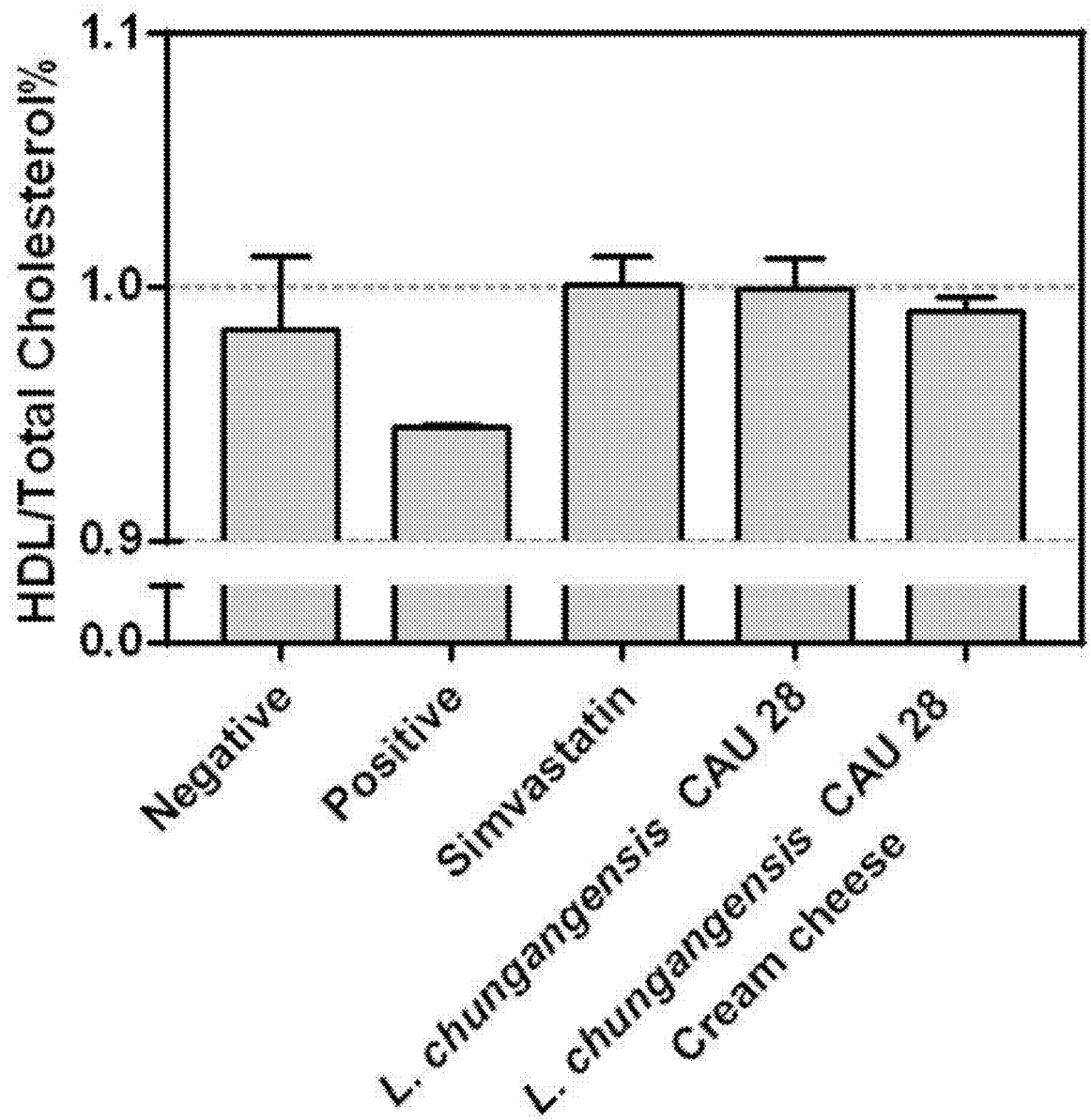
Figure 8C:
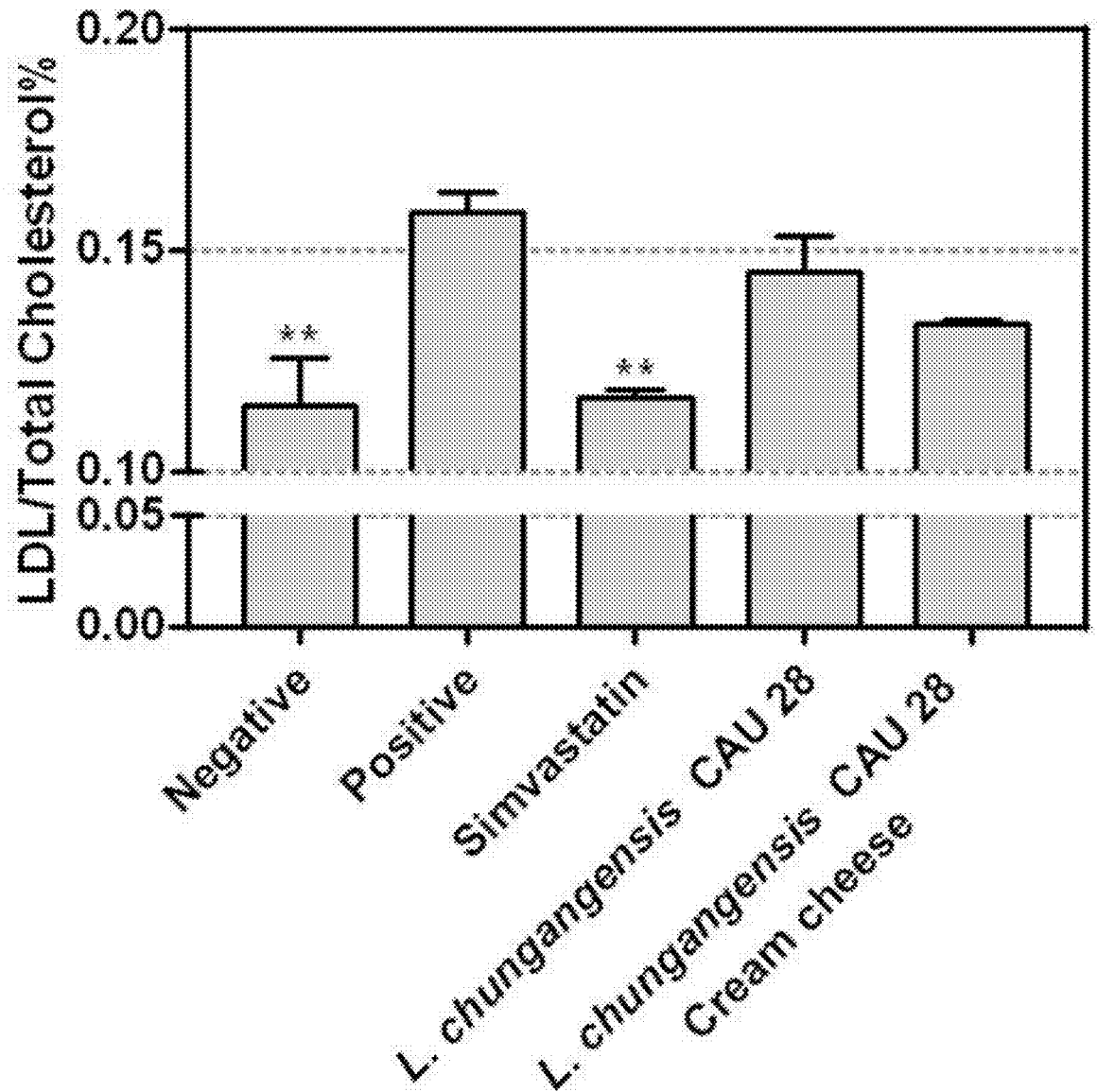
Figure 8D:
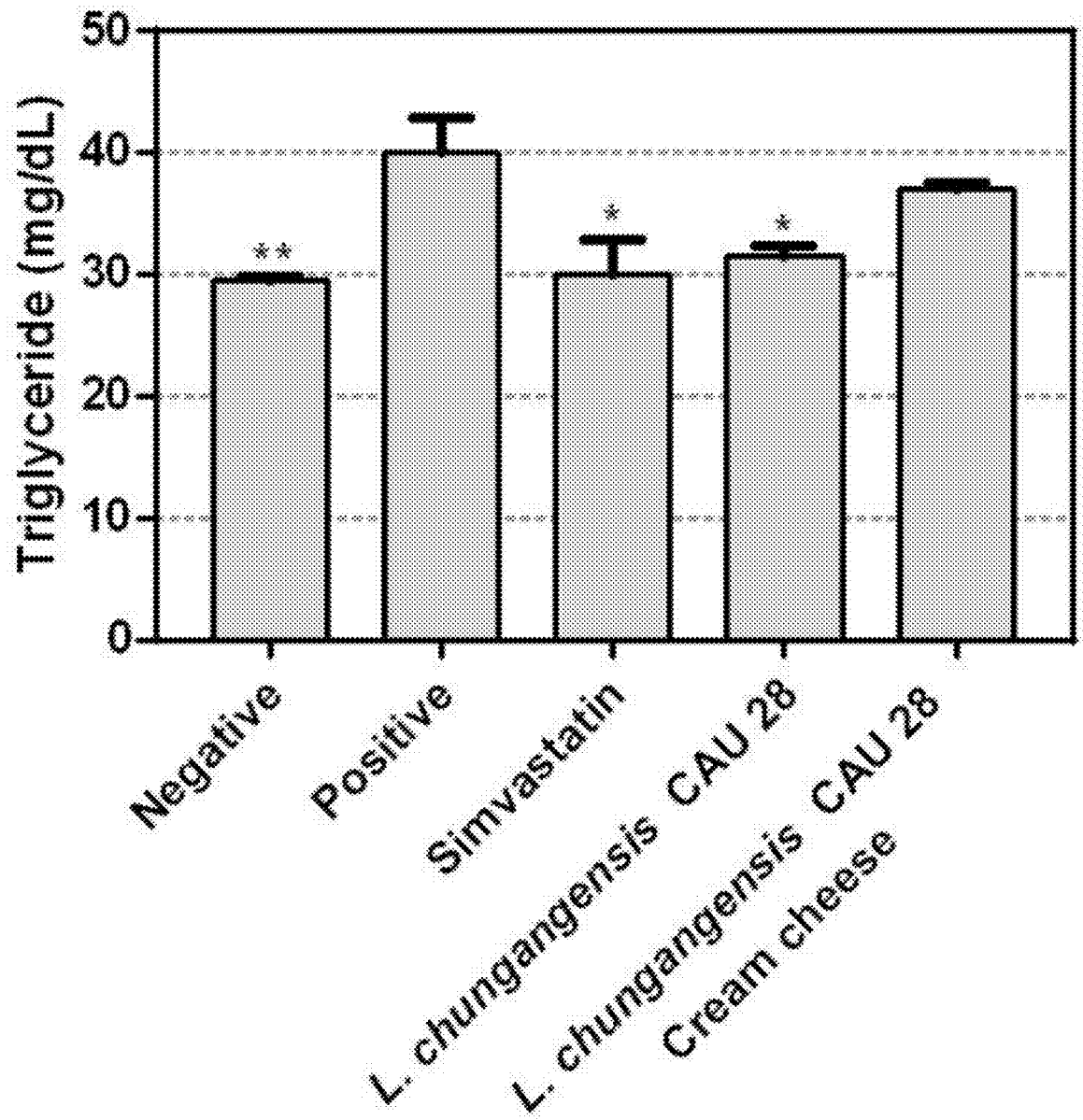

Example 8: Effects of CAU 28 Dry Cells and CAU 28 Cream Cheese Intake on Blood Composition 8-1. Measurement of TC, HDL/TC, LDL/TC and TG Levels After 12 weeks, the serum lipid levels of each group were examined (FIGS. 8a to 8d). As a result, the TC, TG, and LDL/TC values of the negative control group, CAU 28 and CAU 28 cream cheese groups were significantly lower than those of the positive control group (P<0.05) (FIGS. 8a, 8c and 8d). The HDL/TC ratio of the negative control group was higher than the HDL/TC ratio of the positive control group (P=0.2721) (FIG. 8b).

Administration of CAU 28 cream cheese significantly reduced TC (P<0.05) and decreased TG level (P=0.05) compared to the positive control group. In addition, administration of CAU 28 dry cells and simvastatin significantly reduced TC and TG levels in HFD-induced obese mice (P=0.6401) (FIGS. 8a and 8d).

The LDL/TC ratio of the simvastatin, CAU 28 and CAU 28 cream cheese groups was lower than that of the positive control group (FIG. 8c), but the HDL/TC ratio of the positive control group was higher than the HDL/TC ratio of the other experimental groups, but there was no statistical significance (P=0.1295, Table 1) (FIG. 8b).

These results indicate that CAU 28 dry cells and CAU 28 cream cheese intake reduced TC and/or TG serum levels in HFD-induced obese mice.

8-2. Measurement of AST and ALT Levels

Figure 9A:
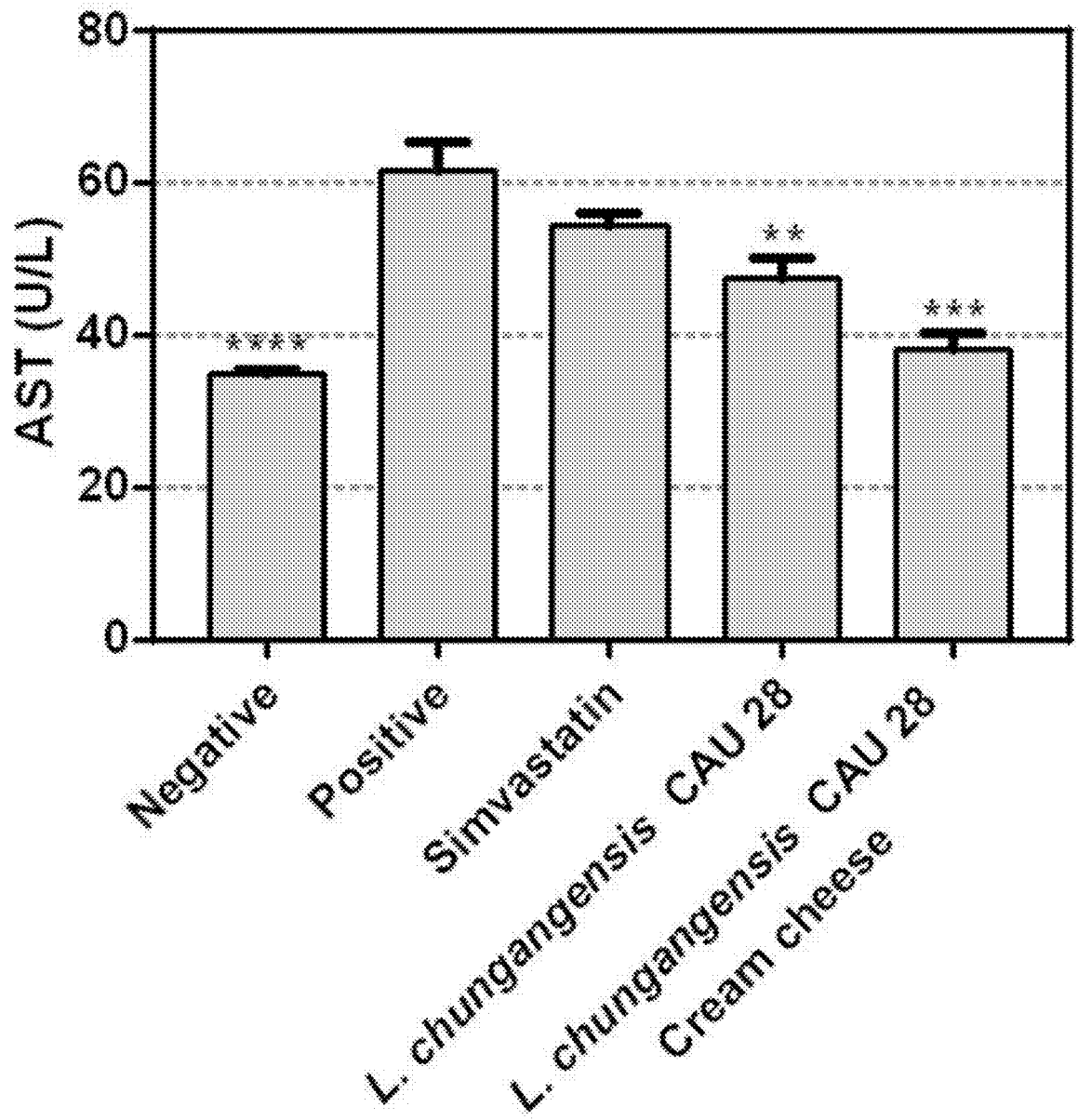
FIGS. 9a and 9b show the effect of oral administration of CAU 28 dry matter and CAU 28 cream cheese on liver disease biomarkers, serum AST (FIG. 9a) and ALT (FIG. 9b) levels are indicated. Differences between means compared to positive controls were assessed using ANOVA. P<0.005, *P<0.0005, ****P<0.0001.

When the structure and function of the cell membrane are destroyed, ALT (Alanine aminotransferase), an enzyme widely present in the cytoplasm of the liver, is released into the blood, so blood ALT levels are frequently used as indicators of liver damage. Serum concentrations of AST and ALT, biomarkers of liver disease, were significantly higher in the positive control group than in the CAU 28 and CAU 28 cream cheese groups (P<0.01) (FIGS. 9a and 9b).

Figure 9B:
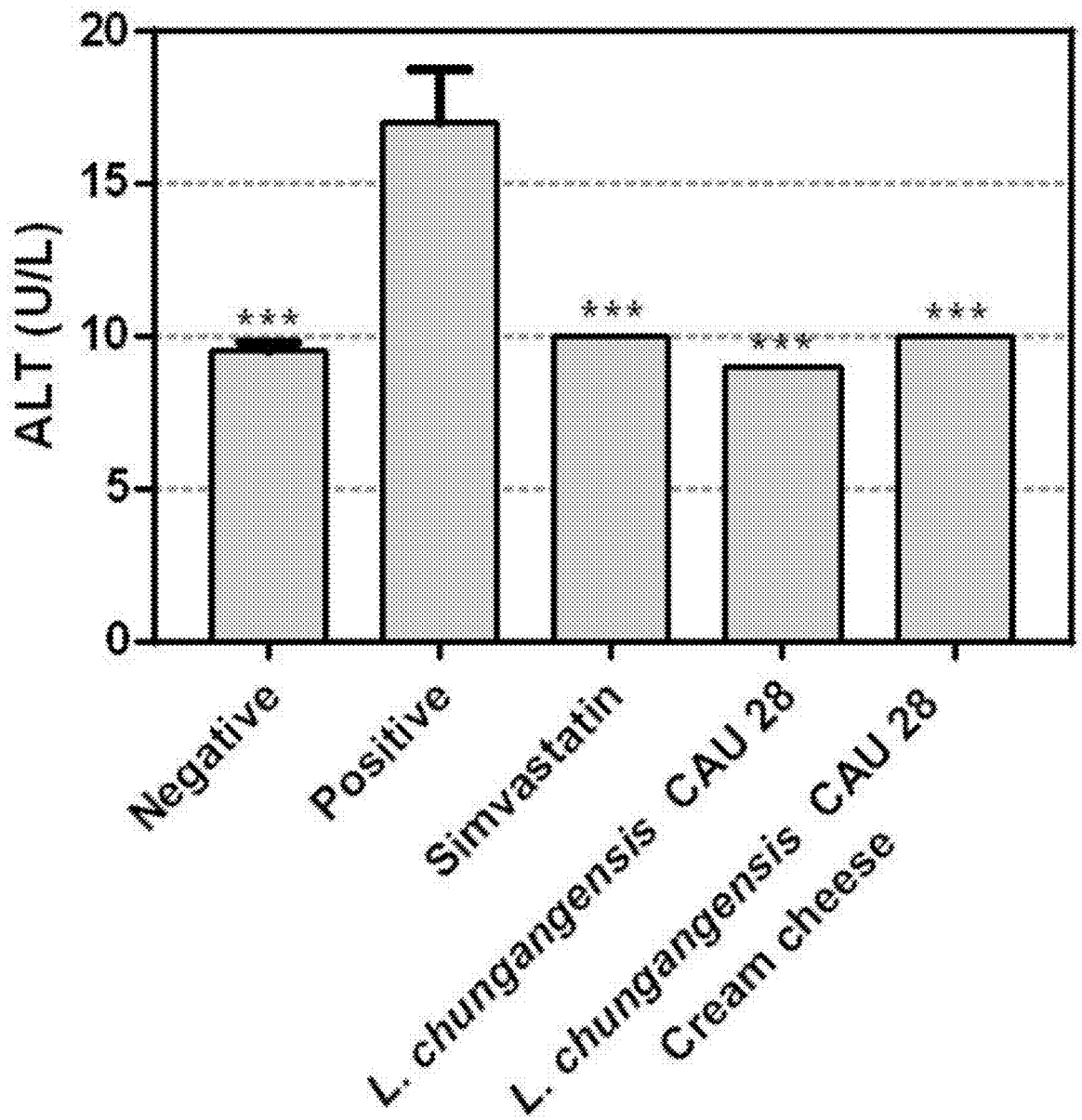

The serum concentration of the positive control group was significantly higher than that of the simvastatin group (P<0.001), but the serum AST concentration of the positive control group and the simvastatin group was not statistically different (P=0.1849) (FIG. 9b).

These results showed that CAU 28 dry cells and CAU 28 cream cheese intake prevented liver damage in HFD-induced obese mice.

Example 9: Effect of CAU 28 Dry Cells and CAU 28 Cream Cheese Intake on Fecal SCFA Acetic acid and propionic acid are absorbed into the blood and enter the metabolic pathway through the liver. It is speculated that SCFA, mainly propionic acid, improves glucose resistance and inhibits cholesterol synthesis in the liver, and this is probably due to suppressing the increase in serum free fatty acid concentration and improving insulin sensitivity. It was found that the SCFA also affects the expression of PPAR, and the synergistic action of PPAR was found to increase the production of ApoA1, a major component of HDL.

Therefore, the levels of acetic acid and propionic acid, which are short chain fatty acids (SCFAs), were measured in mouse feces after 12 weeks.

Figure 10A:
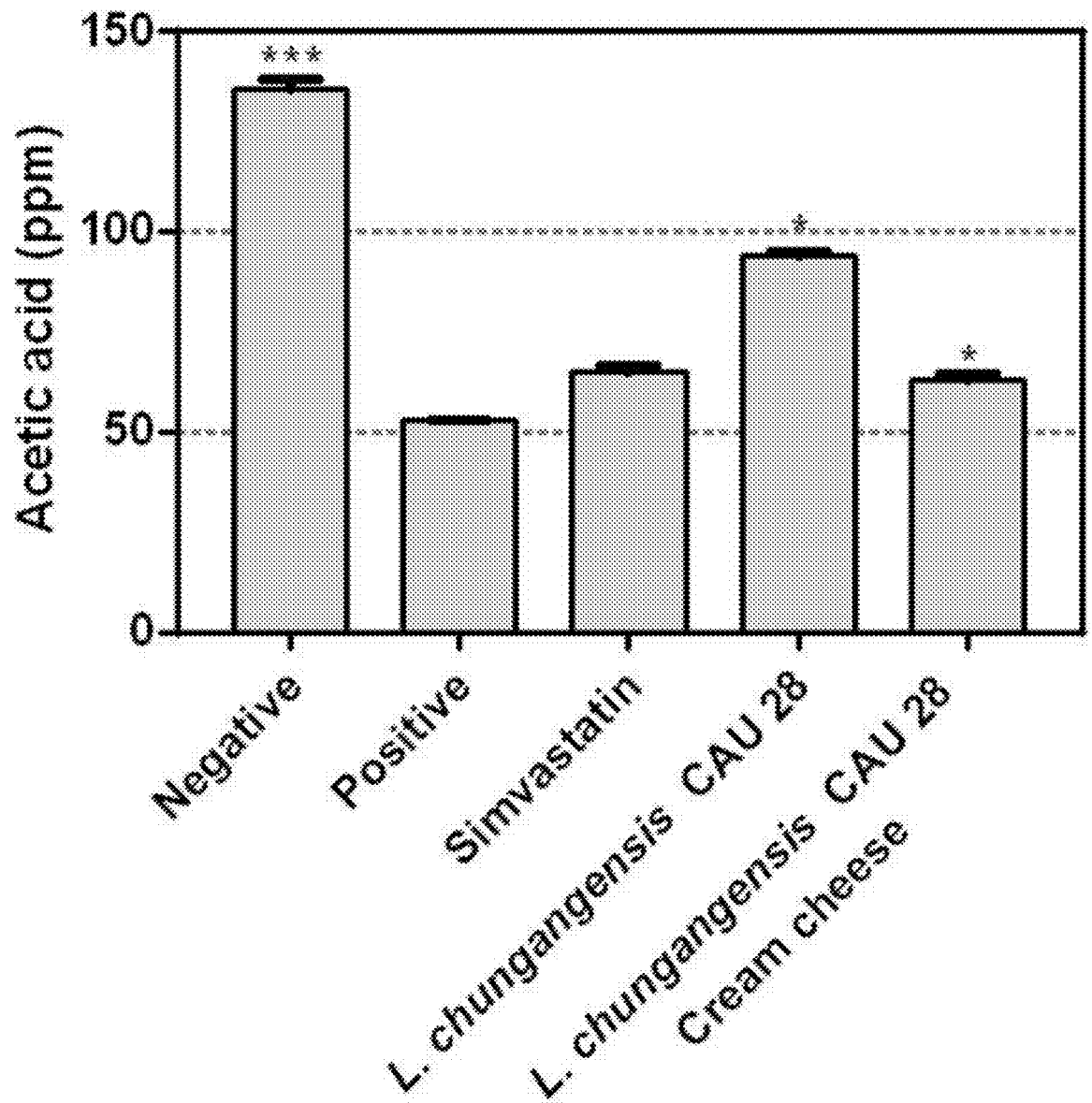
FIGS. 10a and 10b show the effect of oral administration of CAU 28 dry matter and CAU 28 cream cheese on excretory SCFA, excretion levels of acetic acid (FIG. 10a) and propionic acid (FIG. 10b) were measured. Differences between means compared to positive controls were assessed using ANOVA. *P<0.05, *P<0.0005, **P<0.0001.
Figure 10B:
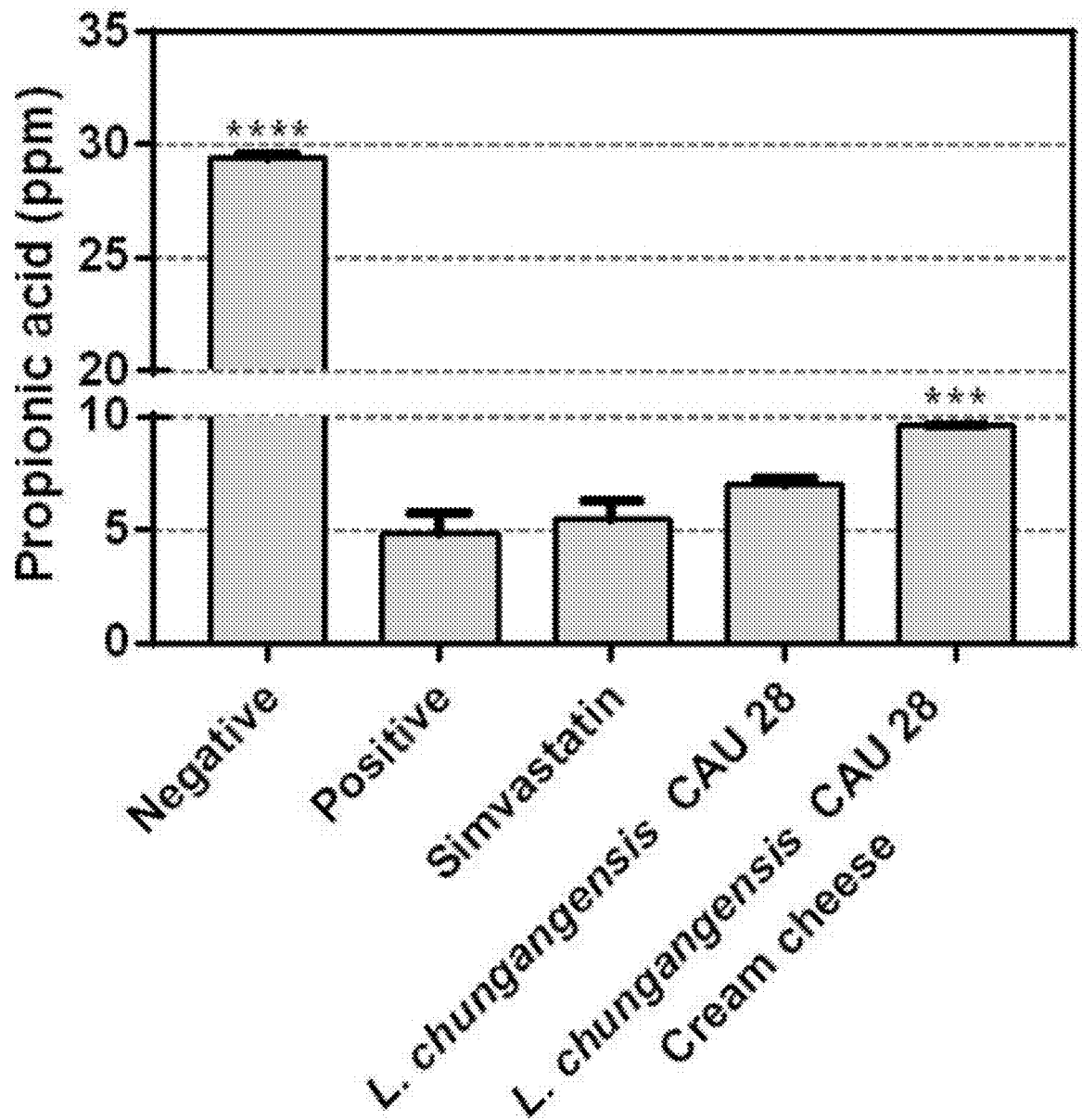

SCFA levels were significantly higher in the negative control group than in the positive control group (P<0.001) (FIGS. 10a and 10b). This indicated that HFD induced a decrease in acetic acid and propionic acid levels in the gut of HFD-induced obese mice.

In addition, the concentrations of acetic acid and propionic acid in the stool were significantly higher in the CAU 28 cream cheese group than in the positive control group (P<0.05). Both acetic acid and propionic acid were higher in the CAU 28 group than in the positive control group (P=0.0749).

These results confirmed that not only had the effect of improving the intestinal flora, but also improved insulin resistance and glucose resistance, and had the effect of inhibiting cholesterol synthesis in the liver as oral administration of CAU 28 dry cells and CAU 28 cream cheese increased the intestinal levels of acetic acid and propionic acid in HFD-induced obese mice.

Example 10: Anti-Obesity Effect and Inhibition of Fat Differentiation of CAU28 Strain on 3T3-L1

When the CAU28 strain for 3T3-L1 was treated, the degree of fat accumulation was quantified, and adipocytes stained with a microscope were confirmed.

Figure 11A:
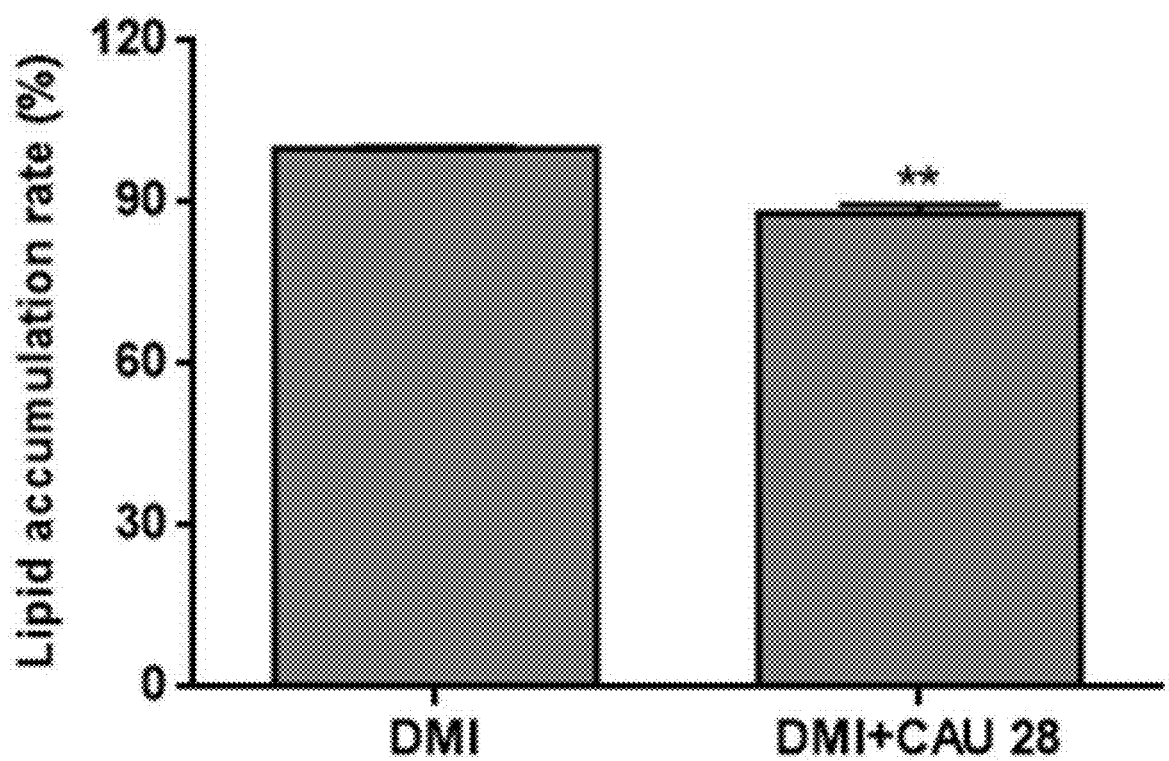
FIGS. 11a and 11b are the results of observing the degree of fat accumulation (FIG. 11a) and adipocytes stained under a microscope (FIG. 11b) when 3T3-L1 adipocyte differentiation was induced and treated with CAU 28 lysate at the same time. *P<0.05, *P<0.0005, **P<0.0001.
Figure 11B:
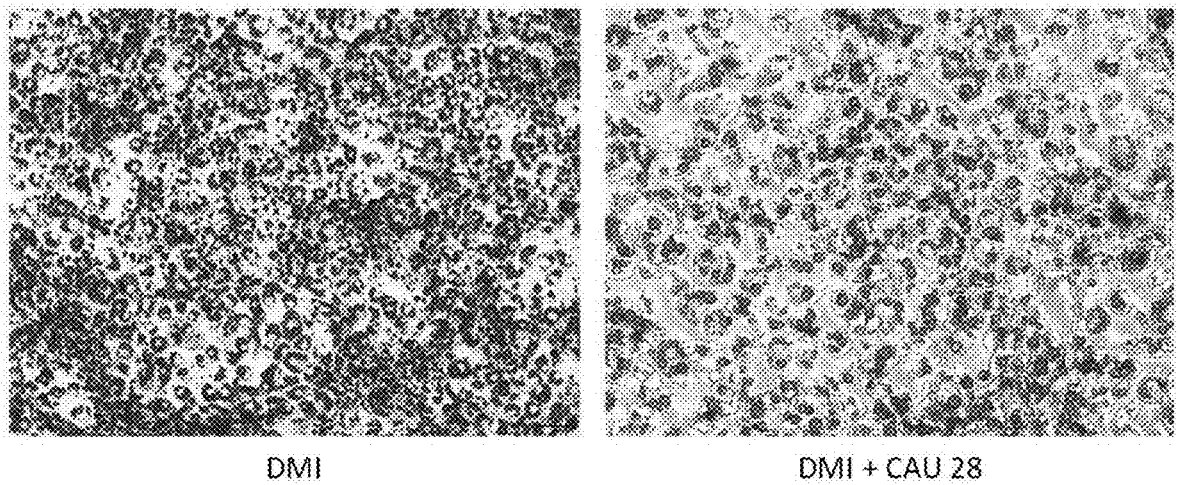

As a result, the degree of fat accumulation was reduced in the experimental group treated with lactic acid bacteria. There was also a statistically significant difference when compared with the positive control group treated with the differentiation component (FIG. 11a). As a result of confirming the stained adipocytes under a microscope, the degree of adipocyte staining was significantly reduced compared to that of the positive control group (FIG. 11b).

Next, when 3T3-L1 was treated with CAU28, mRNA expression levels of fat accumulation-related factors, triglyceride accumulation, and IL-6 secretion were checked.

Figure 12:
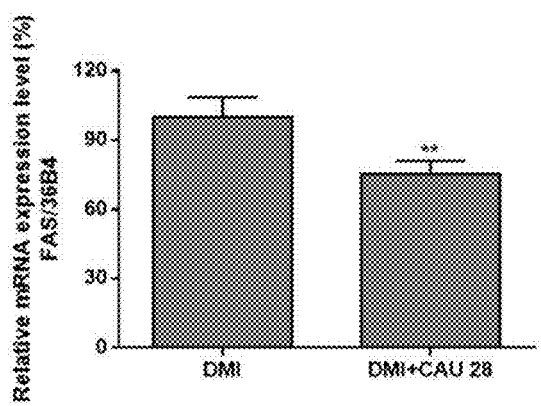
FIG. 12 is the result of evaluating the mRNA expression level of fat accumulation-related factors by real-time PCR when 3T3-L1 adipocyte differentiation is induced and CAU 28 lysate is treated at the same time, and adipocyte differentiation is finished. *P<0.05, *P<0.0005, **P<0.0001.
Figure 12:
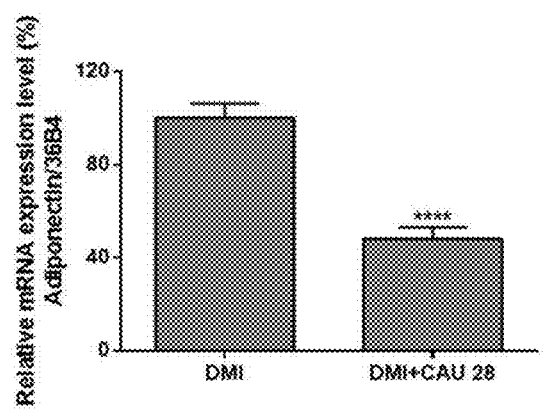
Figure 12:
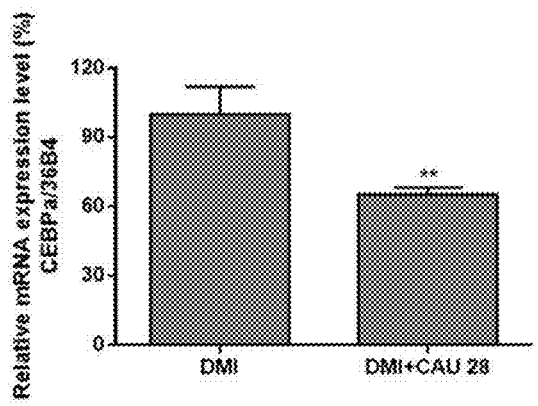
Figure 12:
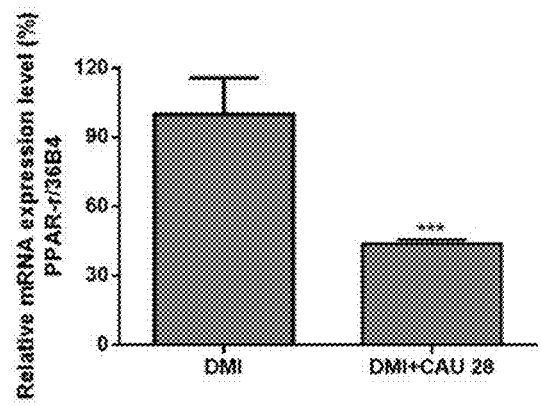
Figure 13A:
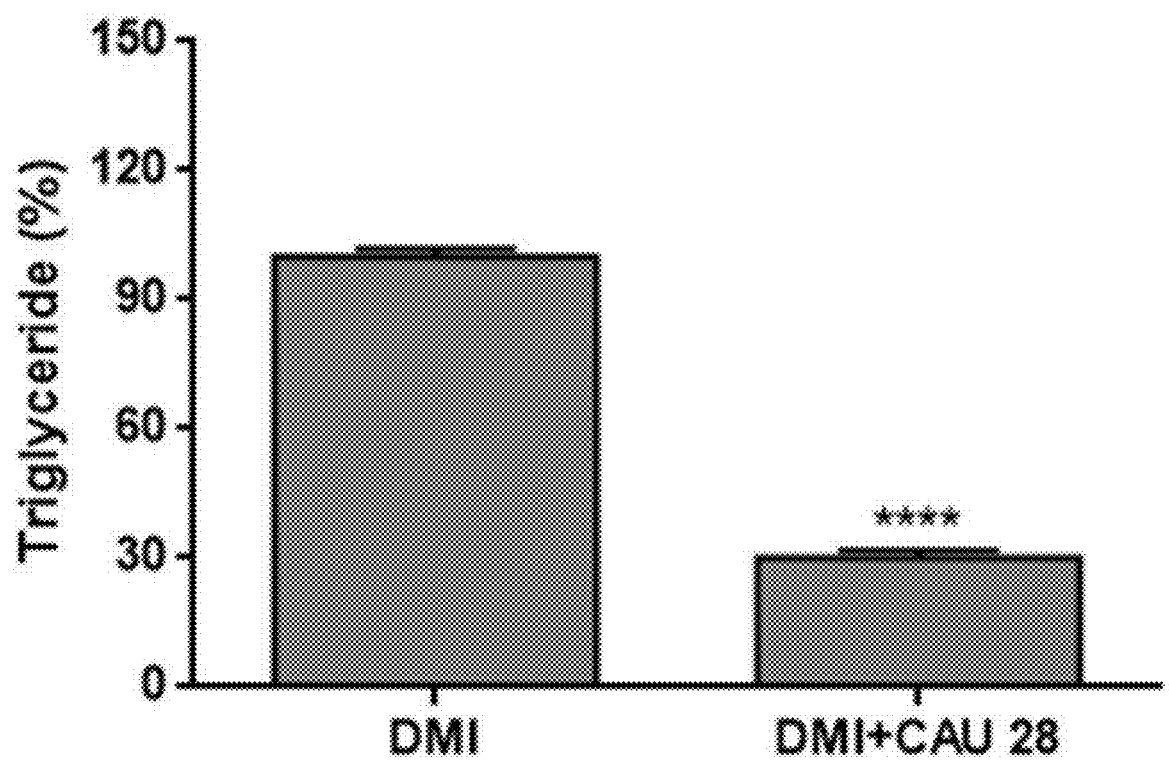
FIGS. 13a and 13b are the results of measuring the degree of accumulation of triglyceride in adipocytes (FIG. 13a) and the amount of IL-6 secreted from adipocytes (FIG. 13b) when 3T3-L1 adipocyte differentiation was induced and CAU 28 lysate was treated at the same time. *P<0.05, *P<0.0005, **P<0.0001.
Figure 13B:
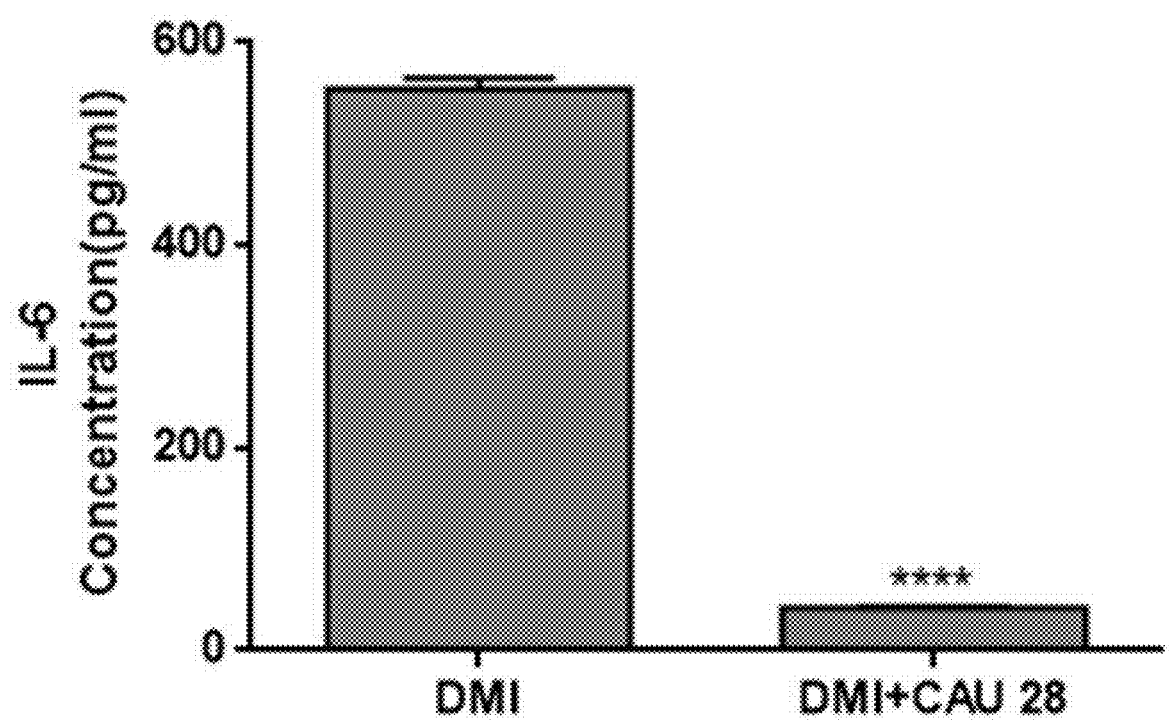

As a result, the experimental group treated with CAU28 showed a decrease in the expression level of fat accumulation-related factors compared to the positive control group, and there was a statistically significant difference (FIG. 12). In addition, the amount of triglyceride accumulated in adipocytes was decreased (FIG. 13a), and it was confirmed that the secretion amount of IL-6 was also significantly decreased (FIG. 13b).

INDUSTRIAL APPLICABILITY

*Lactococcus chungangensis* strain, as a therapeutic composition comprising at least one selected from the group consisting of a culture of the strain and a fermented product of the strain as an active ingredient to prevent and treat fatty liver or metabolic syndrome, has excellent industrial applicability as it can be usefully used for the prevention or development of therapeutic agents for fatty liver or metabolic syndrome because it reduces blood glucose levels, has the effect of suppressing weight gain induced by a high-fat diet, has the effect of reducing the fat in the tissues produced by obesity and inhibiting liver damage.

Name of deposit institution: Korean Collection for Type Cultures

Address: Korea Research Institute of Bioscience and Biotechnology, 125 Gwahak-ro, Yuseong-gu, Daejeon 305-806, Republic of Korea.

accession number: KCTC12684BP deposit date: 20140926

What is claimed is:

1. A method for treating fatty liver or metabolic syndrome in a subject in need thereof, the method comprising:
   administering to the subject in need thereof a composition in an amount effective to treat fatty liver or metabolic syndrome,
   wherein the composition comprises at least one active ingredient selected from the group consisting of:
   *Lactococcus chungangensis* (accession number of KCTC 12684BP),
   a culture containing *Lactococcus chungangensis* (accession number of KCTC 12684BP), and
   a fermented material of *Lactococcus chungangensis* (accession number of KCTC 12684BP).

2. The method of claim 1, wherein the metabolic syndrome includes multiple cardiovascular risk factors selected from hyperlipidemia, hypertension, glucose metabolism abnormality, blood coagulation abnormality, obesity, and combinations thereof.

3. The method of claim 2, wherein the multiple cardiovascular risk factors promote development of diabetes mellitus and atherosclerosis and increase a risk of developing cardiovascular disease.

4. The method of claim 1, wherein the metabolic syndrome is characterized by an increase in blood pressure, an increase in plasma glucose, an increase in triglycerides, an increase in low-density lipoprotein cholesterol (LDL) and a decrease in high-density lipoprotein cholesterol (HDL).

5. The method of claim 1, wherein treating the subject for metabolic syndrome decreases a risk of the subject developing a disease or condition selected from high blood pressure, hyperinsulinemia, hyperlipidemia, fatty liver, arteriosclerosis, diabetes, and cardiovascular disease.

6. The method of claim 1, wherein treating the subject for metabolic syndrome decreases a risk of the subject developing a disease or condition selected from insulin resistance syndrome, obesity, and type 2 diabetes caused by insulin resistance.

7. A method for treating fatty liver syndrome in a subject in need thereof, the method comprising:
   administering to the subject in need thereof a composition in an amount effective to treat fatty liver syndrome,
   wherein the composition comprises at least one active ingredient selected from the group consisting of:
   *Lactococcus chungangensis* (accession number of KCTC 12684BP),
   a culture containing *Lactococcus chungangensis* (accession number of KCTC 12684BP), and
   a fermented material of *Lactococcus chungangensis* (accession number of KCTC 12684BP).

* * * * *